United States Patent [19]

Antoine et al.

[11] Patent Number: 4,970,213

[45] Date of Patent: Nov. 13, 1990

[54] BENZO(1,8)NAPHTHYRIDINE DERIVATIVES AS INTERMEDIATES

[75] Inventors: Michel Antoine, Paris; Michel Barreau, Montgeron; Jean-Francois Desconclois, Paris; Philippe Girard, Arpajon; Guy Picaut, Chevilly Larue, all of France

[73] Assignee: Rhone-Poulenc Sante, Antony, France

[21] Appl. No.: 465,329

[22] Filed: Jan. 16, 1990

[30] Foreign Application Priority Data

Jan. 16, 1989 [FR] France ................... 89 00430
Jul. 28, 1989 [FR] France ................... 89 10220

[51] Int. Cl.$^5$ ............. C07D 471/04; A61K 31/435
[52] U.S. Cl. ........................... 514/292; 546/81
[58] Field of Search ..................... 546/81; 514/292

[56] References Cited

U.S. PATENT DOCUMENTS 4,133,885  1/1979  Bolhofer et al. ............... 544/127
4,229,456 10/1980  Bolhofer et al. ............... 544/127

FOREIGN PATENT DOCUMENTS 0132845  7/1984  European Pat. Off. ............ 546/123
3302126  7/1984  Fed. Rep. of Germany ...... 546/118

OTHER PUBLICATIONS

Chem. Abstr. vol. 61, No. 9, No. 10666g. Oct. 1964.

Primary Examiner—Alan L. Rotman
Assistant Examiner—Joseph K. McKane
Attorney, Agent, or Firm—Stevens, Davis, Miller & Mosher

[57] ABSTRACT

New benzo[b][1,8]naphthyridine derivatives of general formula (I) in which R is a hydrogen atom or an alkyl, fluoroalkyl, cycloalkyl (3 to 6 C), alkoxy, alkylamino or protected alkylamino radical, Hal is F, Cl or Br if R' is hydrogen, or Hal and R' are F, and Alk is an alkyl radical, and their preparation.

These new products can be used as intermediates for the preparation of biologically active products.

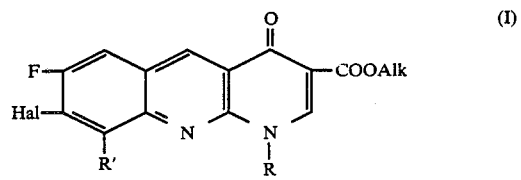

7 Claims, No Drawings

BENZO(1,8)NAPHTHYRIDINE DERIVATIVES AS INTERMEDIATES

The present invention relates to new benzo[b][1,8]-naphthyridine derivatives of general formula:

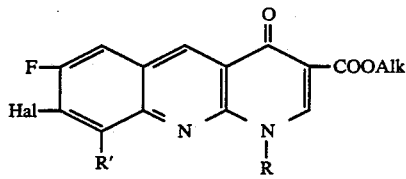

and their preparation.

Naphthyridine derivatives of structure:

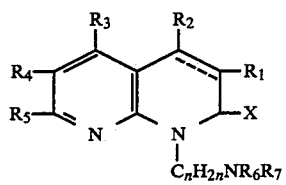

in which X can be oxygen and two adjacent radicals of the radicals $R_1$ to $R_5$ can form a benzene ring, have been described in U.S. Pat. Nos. 4,229,456 and 4,133,885.

These products are used as gastric acid secretion inhibitors.

German patent application No. 3,302,126 describes hypotensive agents of general formula:

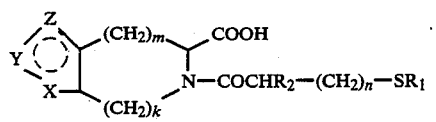

in which the radicals X, Y and Z can be O or a $NR_4$ radical or $CR_5=CR_5$ radical in which the $R_5$s can form a benzene ring.

In the general formula (I):
R represents a hydrogen atom or an alkyl or fluoroalkyl radical, a cycloalkyl radical containing 3 to 6 carbon atoms, or an alkoxy, alkylamino or protected alkylamino radical, Hal is a fluorine, chlorine or bromine atom if R' is a hydrogen atom, or Hal and R' simultaneously represent a fluorine atom, and Alk is an alkyl radical,
it being understood that the alkyl radicals are straight-chain or branched and contain 1 to 4 carbon atoms.

The benzo[b][1,8]naphthyridine ester derivative of general formula (I) can be prepared: either by the action of 3-amino-1,2,4-triazine (to obtain a product for which R is a hydrogen atom), or by the action of a product of general formula:

$$R_2—NH_2 \quad \text{(II)}$$

in which R is alkyl, fluoroalkyl, cycloalkyl, alkylamino or protected alkylamino, on a quinoline derivative of general formula:

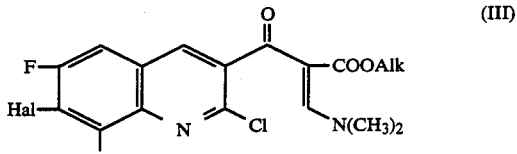

in which Alk and Hal are defined as above, followed by the action of an acid acceptor.

In general, the reaction of 3-amino-1,2,4-triazine or of the product of general formula (II) is carried out in an organic solvent such as an alcohol (ethanol or methanol for example) or a chlorinated solvent (trichloromethane for example) at a temperature of between 10° and 25° C.

The cyclization is carried out, in particular, in the presence of a nitrogenous base (for example triethylamine, or an excess of the amine employed) or of 1,8-diazabicyclo[5.4.0]undec-7-ene in a straight-chain or branched alcohol containing 1 to 4 carbon atoms, at a temperature of between 20° C. and the reflux temperature of the reaction mixture.

The quinoline derivative of general formula (III) can be obtained from the keto-ester of general formula:

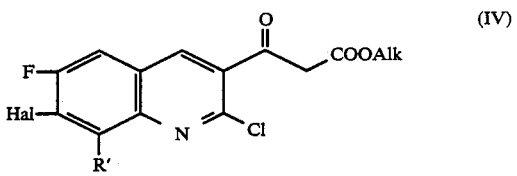

in which Alk, Hal and R, are defined as above, by the action of a N,N-dimethylformamide acetal of general formula:

$$(CH_3)_2N—CH(OAlk_1)_2 \quad \text{(V)}$$

in which $Alk_1$ is a straight-chain or branched alkyl radical containing 1 to 4 carbon atoms.

The reaction is generally carried out in an organic solvent such as an ester (ethyl acetate for example) at a temperature of between 60° and 75° C.

The keto-ester of general formula (IV) in which R' is a hydrogen atom can be obtained from 2,7-dichloro-6-fluoroquinoline-3-carboxylic acid or 2-chloro-6,7-difluoroquinoline-3-carboxylic acid as described below in Examples 1 and 8 or from 7-bromo-2-chloro-6-fluoroquinoline-3-carboxylic acid by analogy with this method. In this case, the 3-bromo-4-fluoroaniline used as starting material can be prepared by the method described by W. B. AUSTIN et al., J. Org. Chem., 46 (11), 2280 (1981).

The keto-ester of general formula (IV) in which R' is a fluorine atom can be obtained from 2-chloro-6,7,8-trifluoroquinoline-3-carboxylic acid as described below in Example 12.

The new products of general formula (I) are used as intermediates for the preparation of benzo[1,8]naphthyridine derivatives of general formula:

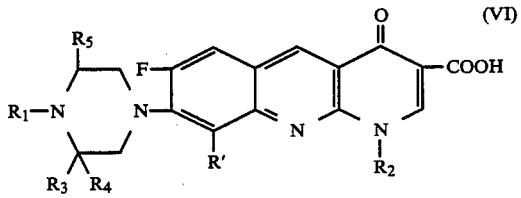

in which:

R₁ represents a hydrogen atom or an alkyl or hydroxyalkyl radical,

R₂ represents a hydrogen atom or an alkyl or fluoroalkyl radical, a cycloalkyl radical containing 3 to 6 carbon atoms, or an alkoxy or alkylamino radical, R₃ represents a hydrogen atom or an alkyl radical, and R₄ and R₅ are different and represent a hydrogen atom or an alkyl radical, or R₃ is a hydrogen atom or an alkyl or cycloalkyl radical and R₄ and R₅ are hydrogen atoms, and R' is a hydrogen or fluorine atom, the alkyl radicals being straight-chain or branched and containing 1 to 4 carbon atoms, as well as their salts and, where appropriate, their isomers, display a particularly valuable antibacterial activity.

The products of general formula (VI) can exist in the hydrated form and it is understood that these hydrates can also be obtained from products of general formula (I).

The benzonaphthyridine derivatives of general formula (VI) can be prepared from products of general formula (I) by working in the following manner.

An acid of general formula:

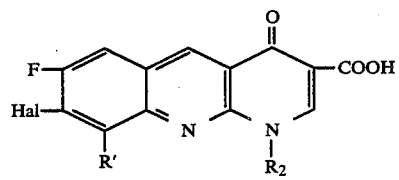

in which R', R₂ and Hal are defined as above, is prepared by any method known for obtaining an acid from an ester, without touching the remainder of the molecule.

The preparation of the acid from the ester generally takes place by acid hydrolysis. The reaction is advantageously carried out in an acetic acid/hydrochloric acid mixture, in sulphuric acid or in methanesulphonic acid at a temperature of between 60° and 100° C. It is also possible to carry out the preparation by saponification in the presence of potassium hydroxide or sodium hydroxide in an aqueous-alcoholic medium at a temperature of between 20° and 80° C.

When the radical R in the benzonaphthyridine derivative of general formula (I) is a protected alkylamino radical, the protective group can be removed either simultaneously with the hydrolysis of the ester (formyl for example) or separately before or after the hydrolysis.

A piperazine derivative of general formula:

in which R₁, R₃, R₄ and R₅ are defined as above, is then reacted with the acid derived from benzo[b][1,8]naphthyridine, of general formula (VII), obtained above and then, if appropriate, if R₁ is a hydrogen atom and if it is desired to obtain a benzo[b][1,8]naphthyridine derivative in which R₁ is methyl, the product obtained is converted to a 8-(4-methyl-1-piperazinyl)-benzo[b]naphthyridine.

The action of the piperazine derivative of general formula (VIII) generally takes place in the presence of an excess of this derivative as an acid acceptor or in the presence of an organic or inorganic acid acceptor in suitable organic solvents. It is possible to carry out the reaction with or without solvents, at a temperature between 30° and 120 C. When it is carried out in the presence of a solvent, the reaction advantageously takes place in solvents such as pyridine, dimethylformamide, dimethyl sulphoxide or acetonitrile.

It is understood that, in the case where the symbol R₂ in the product of general formula (VII) is a hydrogen atom, it is preferable to protect this product beforehand. The protection and the removal of the protective radical after the reaction take place according to customary methods.

The protection can be effected by any group which is compatible and the use and removal of which do not alter the remainder of the molecule. In particular, the methods described by T. W. GREENE, Protective Groups in Organic Synthesis, A. Wiley-Interscience Publication (1981), or by McOMIE, Protective Groups in Organic Chemistry, Plenum Press (1973) are used.

By way of example, the protective groups can be chosen from the trimethylsilyl, trityl, benzhydryl, tetrahyropyrannyl, formyl, acetyl, chloroacetyl, trichloroacetyl, trifluoroacetyl, methoxycarbonyl, ethoxycarbonyl, t.-butoxycarbonyl, trichloroethoxycarbonyl, methoxymethyl and ethoxymethyl radicals.

Where appropriate, the subsequent operation for methylation of the piperazinyl radical advantageously takes place by the action of formaldehyde in the presence of formic acid. The reaction is generally carried out in an aqueous medium at a temperature of between 90° and 100° C.

The benzo[b][1,8]naphthyridine derivatives of general formula (VI) can also be obtained by preparing the corresponding ester of general formula:

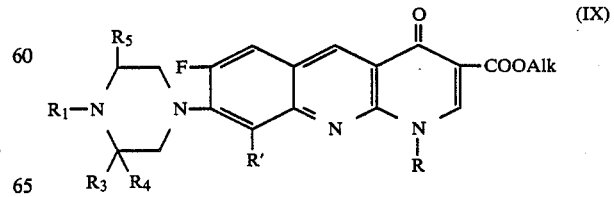

in which R, R', R₁, R₃, R₄, R₅ and Alk are defined as above, from the benzo[b]naphthyridine derivative of general formula (I) by substitution with a piperazine derivative of general formula (VIII).

The reaction is advantageously carried out under the conditions described above for obtaining a product of general formula (VI) from a piperazine derivative of general formula (VIII) and a benzo[b][1,8]naphthyridine derivative of general formula (VII).

The ester of general formula (IX) is then converted to an acid of general formula (VI) by any method known for obtaining an acid from an ester without touching the remainder of the molecule and then, where appropriate, the protective group is removed from the alkylamino radical R and/or, if a product of general formula (VI) in which $R_1$ is a hydrogen atom has been obtained and if it is desired to obtain the corresponding product in which $R_1$ is methyl, the product obtained is converted to a 8-(4-methyl-1-piperazinyl)-benzo[b]naphthyridine derivative.

In particular, the reaction is carried out under the conditions described above for obtaining an acid of general formula (VII) from an ester of general formula (I).

Where appropriate, the methylation of the piperazinyl radical is carried out as described above.

The new products according to the present invention and the products of general formula (VI) can, if necessary, be purified by physical methods such as crystallization or chromatography.

The products of general formula (VI) can be converted to metal salts or addition salts with nitrogenous bases by the methods known per se. These salts can be obtained by the action of a metal (for example alkali metal or alkaline earth metal)-containing base, ammonia or an amine on a product of general formula (VI) in an appropriate solvent, such as an alcohol, an ether or water, or by an exchange reaction with a salt of an organic acid. The salt formed precipitates, after concentration of its solution if necessary; it is separated off by filtration, decanting or lyophilization.

The products of general formula (VI) can also be converted to acid addition salts. The products of general formula (VI) obtained in the form of these salts can be liberated and converted to salts of other acids by customary methods.

The following may be mentioned as examples of pharmaceutically acceptable salts: the salts with the alkali metals (sodium, potassium, lithium) or with the alkaline earth metals (magnesium, calcium), the ammonium salt, the salts of nitrogenous bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine, dibenzylamine) and the addition salts with inorganic acids (hydrochlorides, hydrobromides, sulphates, nitrates, phosphates) or organic acids (succinates, fumarates, maleates, p-toluenesulphonates).

The benzo[b][1,8]naphthyridine derivatives of general formula (VI) and their pharmaceutically acceptable salts have particularly valuable antibacterial properties. They display a remarkable in vitro and in vivo activity on Gram-positive germs and, in a general manner, on the germs responsible for the majority of the infections of the upper and lower air passages.

In vitro, they have been shown to be active at a concentration of between 0.12 and 50 µg/cm$^3$ on *Staphylococcus aureus* IP 8203.

In vivo, they have been shown to be active against experimental infections of mice with *Staphylococcus aureus* IP 8203 at doses of between 2 and 150 mg/kg administered orally or subcutaneously.

Another valuable characteristic of the products of general formula(VI) is their low toxicity. Their $LD_{50}$ is generally greater than 500 mg/kg when administered subcutaneously to mice.

Products of general formula (I) of particular interest are those in which

R is a hydrogen atom, a straight-chain or branched alkyl radical containing 1 to 4 carbon atoms, or a fluoroethyl, cyclopropyl, methoxy or protected methylamino radical, Hal is a fluorine or chlorine atom and R' is a hydrogen atom, or Hal and R' are simultaneously fluorine atoms and Alk is an ethyl radical.

And amongst these products the following products are very particularly interesting:

8-chloro-3-ethoxycarbonyl-7-fluoro-1-methyl-4-oxo-1,4-dihydro-benzo[b][1,8]naphthyridine;

3-ethoxycarbonyl-7,8-difluoro-1-methyl-4-oxo-1,4-dihydro-benzo[b][1,8]naphthyridine;

3-ethoxycarbonyl-7,8-difluoro-1-methoxy-4-oxo-1,4-dihydro-benzo[b][1,8]naphthyridine;

3-ethoxycarbonyl-1-cyclopropyl-7,8-difluoro-4-oxo-1,4-dihydro-benzo[b][1,8]naphthyridine;

3-ethoxycarbonyl-1-methyl-4-oxo-7,8,9-trifluoro-1,4-dihydro-benzo[b][1,8]naphthyridine.

The following examples, which are given as non-limiting examples, illustrate the present invention.

EXAMPLE 1

Methylamine is bubbled into a stirred suspension of 19.3 g of ethyl 2-(2,7-dichloro-6-fluoro-quinoline-3-carbonyl)-3-dimethylaminoacrylate in 250 cm$^3$ of ethanol, kept at between 10° and 15° C., until 16 g of gas have been absorbed. The temperature is allowed to rise to about 20° C., 0.8 g of 1,8-diazabicyclo[5.4.0]undec-7-ene (DBU) is added and the mixture is heated to a temperature close to 75° C. for 2 hours. After cooling to about 20° C., the product is drained and washed with twice 150 cm$^3$ of ethanol and twice with 100 cm$^3$ of diethyl ether. 15 g of 8-chloro-3-ethoxycarbonyl-7-fluoro-1-methyl-4-oxo-1,4-dihydro-benzo[b][1,8]-naphthyridine are obtained in the form of a yellow solid melting at 360°–362° C.

The ethyl 2-(2,7-dichloro-6-fluoro-quinoline-3-carbonyl)-3-dimethylaminoacrylate is prepared in the following manner:

A suspension of 16.5 g of ethyl 3-(2,7-dichloro-6-fluoro-3-quinolyl)-3-oxopropionate in 160 cm$^3$ of ethyl acetate and 19 cm$^3$ of N,N-dimethylformamide dimethyl acetal is heated at a temperature close to 75° C., with stirring, for 2 hours. The reaction mixture is concentrated to dryness under reduced pressure (20 kPa) at 50° C. The dry extract is taken up in 50 cm$^3$ of diisopropyl ether, drained and washed with twice 10 cm$^3$ of diisopropyl ether. 16.57 g of ethyl 2-(2,7-dichloro-6-fluoro-quinoline-3-carbonyl)-3-dimethyl aminoacrylate are obtained in the form of an orange solid melting at 122° C. This product is used for the subsequent steps without further purification.

The ethyl 3-(2,7-dichloro-6-fluoro-3-quinolyl)-3-oxopropionate is prepared in the following manner:

A suspension of 38.75 g of 2,7-dichloro-6-fluoroquinoline-3-carboxylic acid in 410 cm$^3$ of trichloromethane and 24 cm$^3$ of thionyl chloride is heated at a temperature close to 60° C., with stirring, for 6 hours. The solution obtained is concentrated to dryness under reduced pressure (20 kPa) at 50° C. The dry extract is twice taken up in a total of 200 cm$^3$ of toluene and again concentrated under reduced pressure under the same conditions as above. The yellow solid obtained, which melts at 124° C., is dissolved in 230 cm$^3$ of anhydrous tetrahydrofuran. The solution obtained is introduced dropwise, with stirring, in the course of 30 minutes, at between 5° and 10° C., into 200 cm$^3$ of a solution of magnesium chelate in tetrahydrofuran, the preparation of which is described below. The temperature is allowed to rise to 20° C. and the mixture is stirred for 1 hour and a half at this temperature. The solution obtained is introduced dropwise, with vigorous stirring, at a temperature close to 5° C., into 1 liter of 0.5 N sulphuric acid. The temperature of the suspension obtained is allowed to rise to 20° C. and the suspension is stirred for a further 2 hours at this temperature. The suspension is extracted with 1 liter of ethyl acetate and the organic and aqueous phases are filtered through diatomaceous silica for filtration, which enables a small amount of insoluble matter to be removed, and the aqueous phase is extracted twice more with 500 cm$^3$ of ethyl acetate. The combined organic extracts are washed with twice 500 cm$^3$ of water, dried over magnesium sulphate and filtered and the filtrate is concentrated to dryness under reduced pressure (20 kPa) at 40° C. The residue is taken up in 100 cm$^3$ of diisopropyl ether at 20° C., drained and washed with twice 30 cm$^3$ of diisopropyl ether. 40.55 g of ethyl 3-(2,7-dichloro-6-fluoro-3-quinolyl)-3-oxopropionate are obtained in the form of a beige solid melting at 112°-114° C. This product is used for the subsequent steps without further purification.

Preparation of the magnesium chelate of ethyl monomalonate:

5 cm$^3$ of absolute ethanol, 0.2 cm$^3$ of tetrachloromethane and 2 g of ethyl monomalonate are added progressively to 6.9 g of magnesium turnings. After heating, a solution of 23.8 g of ethyl monomalonate in 450 cm$^3$ of ethanol is added in the course of 15 minutes. The mixture is heated at a temperature close to 78° C. for 20 hours and concentrated under reduced pressure (20 kPa) at 50° C. The residue is taken up in twice 100 cm$^3$ of toluene and concentrated under reduced pressure under the same conditions as above. The grey powder obtained is brought into solution by adding anhydrous tetrahydrofuran so as to obtain a total volume of 200 cm$^3$.

The ethyl monomalonate was prepared by the method described by D. S. Breslow, E. Baumgarten, C. R. Hauser., J. Am. Chem. Soc., 66, 1287 (1944) and distilled under reduced pressure (boiling point=132° C./2.7 kPa).

The 2,7-dichloro-6-fluoroquinoline-3-carboxylic acid is prepared in the following manner:

A solution of 89.3 g of potassium permanganate in 1.4 liters of water is added in the course of 1 hour and while keeping the temperature between 10° and 14° C. to a stirred suspension, cooled to 10° C., of 69.5 g of 2,7-dichloro-6-fluoro-3-formyl-1,4-dihydroquinoline in 282 cm$^3$ of 2 N aqueous potassium hydroxide solution and 282 cm$^3$ of water. The temperature is allowed to rise to about 20° C. and the mixture is stirred for a further 30 minutes at this temperature. 26 g of sodium dithionite are added, the mixture is stirred for 10 minutes at a temperature close to 20° C. and filtered through diatomaceous silica for filtration and the filter cake is washed with twice 250 cm$^3$ of water. The filtrate and the aqueous washing phases are combined and 90 cm$^3$ of a 35% aqueous solution of hydrochloric acid are added. The precipitate formed is extracted with 4 times 500 cm$^3$ of ethyl acetate. The combined organic extracts are washed with 3 times 500 cm$^3$ of water, dried over magnesium sulphate, filtered and concentrated under reduced pressure (20 kPa) at 50° C. The residue is taken up in 350 cm$^3$ of diethyl ether, drained and washed with twice 200 cm$^3$ of diethyl ether. 45 g of 2,7-dichloro-6-fluoroquinoline-3-carboxylic acid are obtained in the form of a beige solid melting at 230° C. which is used for the subsequent steps without further purification.

The 2,7-dichloro-6-fluoro-3-formyl-1,4-dihydroquinoline was prepared in the following manner:

55.6 cm$^3$ of phosphoryl chloride are added in the course of 30 minutes, with stirring, at between 10 and 15° C., to a mixture of 250 cm$^3$ of trichloromethane and 54 cm$^3$ of dimethylformamide and the mixture is stirred for 1 hour at a temperature close to 20° C. 52 g of 7-chloro-6-fluoro-3,4-dihydrocarbostyril are added progressively, with vigorous stirring, in the course of 10 minutes, at about 20° C. to the solution obtained. The suspension obtained is heated to a temperature close to 60° C. and is kept at this temperature for a further 2 hours, with stirring. The reaction mixture is concentrated under reduced pressure (20 kPa) at 50° C. until a pasty mixture is obtained. A mixture of 250 cm$^3$ of water and 250 g of crushed ice is added, with vigorous stirring. The solid obtained is drained at about 5° C. and washed with 4 times 125 cm$^3$ of water at 5° C. The moist product obtained and 58 g of sodium acetate are added simultaneously, in the course of 1 hour, to 500 cm$^3$ of water at 90° C. in such a way as to maintain the pH at about 6. The mixture is stirred for a further 15 minutes at 90° C., the temperature is allowed to fall to about 50° C. and the product is drained at this temperature and washed with 3 times 250 cm$^3$ of water at about 20° C. 54.3 g of 2,7-dichloro-6-fluoro-3-formyl-1,4-dihydro quinoline are obtained in the form of a yellow solid melting at 260° C. which is used in this form for the subsequent steps.

The 7-chloro-6-fluoro-3,4-dihydrocarbostyril is prepared in the following manner:

350 g of aluminium chloride are added in the course of 5 minutes, with vigorous stirring, to 174.4 g of 3'-chloro-4'-fluoro-3-(N-chloro)-propionanilide. The solid mixture is heated to about 60° C. in the course of 30 minutes. The temperature rises on its own to about 80° C. and the reaction mixture becomes liquid. It is then heated to 110° C. in the course of 15 minutes and kept at between 110° and 120° C. for 3 hours. The reaction mixture (at about 110° C.) is poured, in the course of 10 minutes, with vigorous stirring, into a mixture of 550 cm$^3$ of 35% hydrochloric acid and 500 g of crushed ice. The temperature is allowed to rise to 20° C. and the product is drained and washed with 6 times 500 cm$^3$ of water.

The moist product is recrystallized from 1.2 liters of ethanol. 108 g of 7-chloro-6-fluoro-3,4-dihydrocarbostyril are obtained in the form of a beige solid melting at 215° C.

The 3'-chloro-4'-fluoro-3-(N-chloro)-propionanilide was prepared in the following manner:

A solution of 127 g of 3-chloropropionyl chloride in 200 cm³ of acetone is added, with stirring, in the course of 35 minutes, to a solution, at a temperature close to 55° C., of 291 g of 3-chloro-4-fluoroaniline in 500 cm³ of acetone and the mixture is kept at this temperature for 2 hours. After cooling to about 20° C., the insoluble matter is removed by filtration and washed with twice 200 cm³ of acetone. The filtrate and the combined washings are poured into 2 liters of water and 1 kg of ice, with stirring. The temperature is allowed to rise to about 20° C. and the mixture is extracted with 4 times 500 cm³ of dichloromethane. The combined organic extracts are washed with 3 times 500 cm³ of water, dried over magnesium sulphate, stirred for 15 minutes with 6 g of Norit vegetable charcoal, filtered through diatomaceous silica for filtration and concentrated under reduced pressure (20 kPa) at 50° C. The solid obtained is recrystallized from a mixture of 133 cm³ of cyclohexane and 67 cm³ of diisopropyl ether. 176 g of 3'-chloro-4'-fluoro-3-(N-chloro)-propionanilide are obtained in the form of a beige solid melting at 94° C., which is used in this form for the subsequent steps.

EXAMPLE 2

16 g of ethylamine are added, in the course of 5 minutes, at between 10° and 15° C., to a stirred suspension of 13.5 g of ethyl 2-(2,7-dichloro-6-fluoroquinoline-3-carbonyl)-3-dimethylaminoacrylate in 135 cm³ of ethanol, the temperature is allowed to rise to about 20° C., 0.5 g of DBU is added and the mixture is heated, with stirring, for 2 hours at a temperature close to 75° C. After cooling to a temperature close to 20° C., the precipitate is drained and washed with twice 100 cm³ of ethanol and twice 100 cm³ of diethyl ether. 10.4 g of 8-chloro-3-ethoxycarbonyl-1-ethyl-7-fluoro-4-oxo-1,4-dihydro-benzo-[b][1,8]naphthyridine are obtained in the form of a yellow solid melting at 300°–301° C.

EXAMPLE 3

The 8-chloro-3-ethoxycarbonyl-7-fluoro-1-(N-formyl-N-methylamino)-4-oxo-1,4-dihydrobenzo [b][1,8]naphthyridine is prepared under the conditions described in Example 1 but starting from 19.25 g of ethyl 2-(2,7-dichloro-6-fluoroquinoline-3-carbonyl)-3-dimethylaminoacrylate, 4.05 g of N-formyl-N-methylhydrazine and 1.6 g of DBU in 200 cm³ of ethanol. 16.4 g of 8-chloro-3-ethoxycarbonyl-7-fluoro-1-(N-formyl-N-methylamino)-4-oxo-1,4-dihy drobenzo [b][1,8]naphthyridine are obtained in the form of a colourless solid melting at 296°–298° C.

The N-formyl-N-methylhydrazine can be prepared by the method described by Carl Th. Pedersen, Acta Chem. Scand., 18(9), 2199 (1964).

EXAMPLE 4

A solution of 20.6 g of ethyl 2-(2,7-dichloro-6-fluoroquinoline-3-carbonyl)-3-dimethylaminoacrylate and 6 g of cyclopropylamine in 100 cm³ of trichloromethane is stirred at a temperature close to 20° C. for 24 hours. The reaction mixture is concentrated under reduced pressure (20 kPa) at 50° C. The residue is taken up in 180 cm³ of ethanol and 10 g of DBU and the solution obtained is heated at a temperature close to 78° C. for 4 hours. After cooling to a temperature close to 20° C., the precipitate obtained is drained and washed with twice 60 cm³ of ethanol. 13.65 g of 8-chloro-1-cyclopropyl-3-ethoxycarbonyl-7-fluoro-4-oxo-1,4-dihydro-benzo[b][1,8]naphthyridine are obtained in the form of a pale yellow solid melting at 256° C., which is used for the subsequent steps without further purification.

EXAMPLE 5

The 8-chloro-3-ethoxycarbonyl-7-fluoro-4-oxo-1-tert.-butyl-1,4-dihydro-benzo [b][1,8]naphthyridine is prepared under the conditions of Example 4 but starting from 8.86 g of ethyl 2-(2,7-dichloro-6-fluoroquinoline-3-carbonyl)-3-dimethylaminoacrylate and 4.03 g of tert.-butylamine in 45 cm³ of trichloromethane and then in 4.53 g of DBU and 45 cm³ of ethanol. 5 g of 8-chloro-3-ethoxycarbonyl-7-fluoro-4-oxo-1-tert.-butyl-1,4-dihydro-benzo[b][1,8]naphthyridine are obtained in the form of a yellow solid melting at 239° C.

EXAMPLE 6

A mixture of 11.3 g of ethyl 2-(2,7,-dichloro-6-fluoroquinoline-3-carbonyl)-3-dimethylaminoacrylate and 5.65 g of 3-amino-1,2,4-triazine in 60 cm³ of trichloromethane is stirred for 16 hours at a temperature close to 20 C. The reaction mixture is concentrated to dryness under reduced pressure (20 kPa) at a temperature close to 30° C. The residue is taken up in 60 cm³ of ethanol and 5.6 g of DBU and the mixture is heated at a temperature close to 75° C. for 20 hours. After cooling to 20° C., the insoluble matter is drained and washed with twice 40 cm³ of ethanol. 6.1 g of 8-chloro-3-ethoxycarbonyl-7-fluoro-4-oxo-1,4-dihydrobenzo [b][1,8]naphthyridine are obtained in the form of a brown solid which decomposes at 378°–380° C. and which can be used for the subsequent steps without further purification.

EXAMPLE 7

2.7 cm³ of triethylamine are added to a suspension of 1.9 g of 2-fluoroethylamine hydrochloride in 25 cm³ of trichloromethane. 3.5 g of ethyl 2-(2,7-dichloro-6-fluoroquinoline-3-carbonyl)-3-di methylaminoacrylate are added to the solution obtained at about 20° C. After stirring at this temperature for 16 hours, the solution is concentrated to dryness under reduced pressure (20 kPa) at about 50° C. The residue is taken up in 20 cm³ of ethanol and 3 cm³ of triethylamine and heat at about 75° C., with stirring for 2 hours. After cooling to about 20° C. the insoluble matter is drained and washed with twice 10 cm³ of ethanol and twice 10 cm³ of diisopropyl ether. 1.9 g of 8-chloro-3-ethoxycarbonyl-7-fluoro-1-(2-fluoro-ethyl)-4-oxo-1,4-di hydro-benzo[b][1,8]naphthyridine are obtained in the form of a yellow solid melting at 268° C., which can be used for the subsequent steps without further purification.

EXAMPLE 8

A stirred suspension of 5.27 g of ethyl 2-(2-chloro-6,7-difluoro quinoline-3-carbonyl)-3-cyclopropylaminoacrylate in 2.22 g of 1,8-diazabicyclo[5.4.0]undec-7-ene (DBU) and 120 cm³ of ethanol is heated at a temperature close to 75° C. for 35 minutes. After cooling to about 20° C., the reaction mixture is taken up in 100 cm³ of water and extracted with once 100 cm³ and twice 50 cm³ of trichloromethane. The combined organic extracts are washed with 3 times 50 cm³ of water, dried over magnesium sulphate, filtered and concentrated under reduced pressure (20 kPa) at a temperature close to 20° C. The dry extract obtained is taken up in 30 cm³ of diisopropyl ether, drained and recrystallized from a mixture of 75 cm³ of ethanol and 75 cm³ of dimethylformamide. 3.57 g of 1-cyclopropyl-3-ethoxycarbonyl-7,8-di fluoro-4-oxo-1,4-dihydro-benzo[b][1,8]naphthyridine are obtained in the form of a yellow solid melting at 229°–230° C.

The ethyl 2-(2-chloro-6,7-difluoroquinoline-3-carbonyl)-3-cyclopropylaminoacrylate is prepared in the following manner:

A solution of 6.25 g of ethyl 2-(2-chloro-6,7-difluoroquinoline-3-carbonyl)-3-dimethylaminoacrylate in 2.91 g of cyclopropylamine and 25 cm³ of trichloromethane is stirred for 3 hours at a temperature close to 20° C. The reaction mixture is concentrated under reduced pressure (20 kPa) at a temperature close to 50° C. The dry extract is taken up in 50 cm³ of diisopropyl ether, drained and then washed with 20 cm³ of the same solvent.

5.27 g of ethyl 2-(2-chloro-6,7-difluoroquinoline-3-carbonyl)-3-cyclopropylaminoacrylate are obtained in the form of an orange solid melting at 116°–117° C. This product is used for the subsequent steps without further purification.

The ethyl 2-(2-chloro-6,7-difluoroquinoline-3-carbonyl)-3-dimethylaminoacrylate is prepared in the following manner:

A suspension of 6.17 g of ethyl 3-(2-chloro-6,7-difluoro-3-quinolyl)-3-oxopropionate in 7.15 g of N,N-dimethylformamide dimethyl acetal and 60 cm³ of ethyl acetate is heated at a temperature close to 75° C. for 1 hour 15 minutes. The reaction mixture is concentrated to dryness under reduced pressure (20 kPa) at about 50° C. The residue is taken up in 50 cm³ of diisopropyl ether, drained and washed with 3 times 25 cm³ of the same solvent. 6.65 g of ethyl 2-(2-chloro-6,7-difluoroquinoline-3-carbonyl)-3-dimethylaminoacrylate are obtained in the form of an orange solid melting at 140° C.

The ethyl 3-(2-chloro-6,7-difluoro-3-quinolyl)-3-oxopropionate is prepared in the following manner:

A suspension of 14.13 g of 2-chloro-6,7-difluoroquinoline-3-carboxylic acid in 29 cm³ of thionyl chloride and 220 cm³ of trichloromethane is heated at a temperature close to 60° C. for 4 hours. The solution obtained is concentrated to dryness under reduced pressure (20 kPa) at about 60° C. The residue obtained is taken up in 75cm³ of n-hexane, drained and washed with twice 60 cm³ of the same solvent. The 14.4 g of yellow solid obtained are poured into solution in 115 cm³ of tetrahydrofuran. This solution is introduced dropwise, with stirring, in the course of 35 minutes, at between 5° and 10° C., into 70 cm³ of a solution of magnesium chelate of ethyl monomalonate in tetrahydrofuran, prepared under the conditions described below. The temperature is allowed to rise to about 20° C. and the mixture is stirred for a further 2 hours under these conditions. The solution obtained is introduced dropwise, with stirring, in the course of 30 minutes, at a temperature close to 5° C., into 560 cm³ of 0.5 N sulphuric acid. The temperature of the suspension obtained is allowed to rise to 20° C. and the suspension is then stirred for a further 1 hour and a half at this temperature. It is extracted with 3 times 250 cm³ of ethyl acetate. The combined organic extracts are washed with twice 250 cm³ of water, dried over magnesium sulphate, filtered and concentrated to dryness under reduced pressure (20 kPa) at 50° C. The residue obtained is taken up in 50 cm³ of n-hexane containing 20% of diisopropyl ether, drained, washed with 10 cm³ of the same mixture and recrystallized from 60 cm³ of isopropanol containing 30% of n-hexane. 11.84 g of ethyl 3-(2-chloro-6,7-difluoro-3-quinolyl)-3-oxopropionate are obtained in the form of a cream solid melting at 107° C.

Preparation of the magnesium chelate of ethyl monomalonate:

2 cm³ of absolute ethanol, 0.1 cm³ of tetrachloromethane and 1 g of ethyl monomalonate are added progressively to 2.78 g of magnesium turnings. After heating, a solution of 9 g of ethyl monomalonate in 180 cm³ of ethanol is added in the course of 15 minutes. The mixture is heated for 20 hours at a temperature close to 75° C. and concentrated under reduced pressure (20 kPa) at 50° C. The residue is taken up in twice 100 cm³ of toluene and the mixture is concentrated under reduced pressure under the same conditions as above. The grey powder obtained is brought into solution by adding anhydrous tetrahydrofuran in an amount to obtain a total volume of 70 cm³.

The 2-chloro-6,7-difluoroquinoline-3-carboxylic acid was prepared in the following manner:

A solution of 115 g of potassium permanganate in 1.215 liters of water is added in the course of 1 hour, while keeping the temperature between 10° and 14° C., to a stirred suspension, cooled to 10° C., of 70.18 g of 2-chloro-6,7-difluoro-3-formyl-1,4-dihy droquinoline in 970 cm³ of N aqueous potassium hydroxide solution. The temperature is allowed to rise to about 20° C. and the mixture is stirred for a further 30 minutes at this temperature. 38.5 g of sodium dithionite are added, the mixture is stirred for 10 minutes at a temperature close to 20° C. and filtered through diatomaceous silica and the filter cake is washed with 3 times 200 cm³ of water. The filtrate and the aqueous washing phases are combined and 140 cm³ of 35% aqueous hydrochloric acid solution are added. The precipitate formed is extracted with 4 times 800 cm³ of ethyl acetate. The combined organic extracts are washed with twice 500 cm³ of water, dried over magnesium sulphate, filtered and concentrated under reduced pressure (20 kPa) at 50° C. The residue is taken up in 400 cm³ of diethyl ether, drained and washed with twice 200 cm³ of the same solvent. 49.2 g of 2-chloro-6,7-difluoroquinoline-3-carboxylic acid are obtained in the form of a beige solid melting at 232° C., which is used for the subsequent steps without further purification.

The 2-chloro-6,7-difluoro-3-formyl-1,4-dihydroquinoline was prepared in the following manner:

76.9 cm³ of phosphoryl chloride are added in the course of 30 minutes, with stirring, at between 10° and 15° C., to a mixture of 800 cm³ of trichloromethane and 74.35 cm³ of dimethylformamide and the mixture is stirred for 1 hour at a temperature close to 20° C. 65.8 g of 6,7-difluoro-3,4-dihydrocarbostyril are added in the course of 10 minutes, at about 20° C., with vigorous stirring, to the solution obtained. The suspension obtained is heated to a temperature close to 60° C. and kept at this temperature for 2 hours. The reaction mixture is concentrated under reduced pressure (20 kPa) at 50° C. until a pasty mixture is obtained. A mixture of 500 g of ice and 500 cm³ of water is added, with vigorous stirring. The solid obtained is drained at about 5° C. and washed with 3 times 300 cm³ of water at 5° C. The moist product obtained and 60 g of sodium acetate are added simultaneously, in the course of 1 hour, to 1.5 liters of water at 90° C., in such a way as to keep the pH at about 6. The mixture is stirred for a further 30 minutes at 90° C., the temperature is allowed to fall to about 50° C. and the product is drained at this temperature and washed with 3 times 300 cm³ of water at about 20° C. 70.18 g of 2-chloro-6,7-difluoro-3-formyl-1,4-dihydroquinoline are obtained in the form of a yellow solid melting at 260° C., which is used in this form for the subsequent steps.

The 6,7-difluoro-3,4-dihydrocarbostyril is obtained in the following manner:

134 g of aluminium chloride are added to 67 g of 3',4'-difluoro-3-(N-chloro)-propionanilide with vigorous stirring and then, after about 2 minutes, a further 135.9 g of 3',4'-difluoro-3-(N-chloro)-propionanilide and 272 g of aluminium chloride are added in small fractions in the course of 15 minutes. The temperature rises on its own to about 60° C. and the reaction mixture becomes liquid. It is then heated to 110° C. in the course of 20 minutes and kept at between 110° and 120° C. for 2 hours. The reaction mixture (at about 110° C.) is poured in the course of 10 minutes, with vigorous stirring, into a mixture of 840 cm³ of 35% hydrochloric acid and 1 kg of crushed ice. The temperature is allowed to rise to about 20° C. and the product is drained and washed with 600 cm³ of water, twice 300 cm³ of ethanol at 5° C. and twice 400 cm³ of diethyl ether at about 20° C. 131.58 g of 6,7-difluoro-1,4-dihydrocarbostyril are obtained in the form of a beige solid melting at 216° C., which is used in this form for the subsequent steps.

The 3',4'-difluoro-3-(N-chloro)-propionanilide is prepared in the following manner:

139.16 g of 3-chloro-propionyl chloride are added, with stirring, in the course of 1 hour and a half to a solution of 125 g of 3,4-difluoroaniline in 80 cm³ of pyridine and 1.5 liters of acetone heated to a temperature close to 55° C. and the mixture is kept at this temperature for 1 hour and a half. After cooling to about 20° C., the solution is poured, with stirring, into a mixture of 1 liter of water and 500 g of crushed ice. The temperature is allowed to rise to about 20° C. and the mixture is extracted with 3 times 500 cm³ of dichloromethane. The combined organic extracts are washed with 500 cm³ of N hydrochloric acid and 5 times 500 cm³ of water, dried over magnesium sulphate, filtered and concentrated under reduced pressure (20 kPa) at about 50° C. The solid obtained is taken up in 500 cm³ of n-hexane, drained and washed with twice 100 cm³ of the same solvent. 202.9 g of 3',4'-difluoro-3-(N-chloro)-propionanilide are obtained in the form of a beige solid melting at 76° C., which is used for the subsequent steps without further purification.

EXAMPLE 9

2.13 g of triethylamine are added to a suspension of 1.7 g of methoxylamine hydrochloride in 40 cm³ of trichloromethane. After stirring for 15 minutes at a temperature close to 20° C., 3.69 g of ethyl 2-(2-chloro-6,7-difluoroquinoline-3-carbonyl)-3-dimethylaminoacrylate are added to the solution obtained and the mixture is stirred for 4 hours and a half at about 20° C. The reaction mixture is concentrated to dryness under reduced pressure (20 kPa) at a temperature close to 50° C. The residue is taken up in 70 cm³ of ethanol and 3.6 g of triethylamine and the mixture is heated for 30 minutes at a temperature close to 75° C. After cooling to about 20° C., the precipitate obtained is drained and washed with 3 times 30 cm³ of ethanol. 2.67 g of 3-ethoxycarbonyl-7,8-difluoro-1-methoxy-4-oxo-1,4-dihydro-benzo[b][1,8]naphthyridine are obtained in the form of a pale yellow solid melting at 266°-268° C.

EXAMPLE 10

A solution, at about 0° C., of 11.3 g of methylamine in 50 cm³ of ethanol is added in the course of 10 minutes, at between 0° and 5° C., to a stirred suspension of 22.3 g of ethyl 2-(2-chloro-6,7-difluoroquinoline-3-carbonyl)-3-dimethylaminoacrylate in 480 cm³ of ethanol, kept at a temperature close to 0° C., the temperature is allowed to rise to about 25° C. and the mixture is stirred for a further 16 hours at the same temperature. The insoluble matter is drained and washed with 3 times 100 cm³ of ethanol and twice 100 cm³ of diethyl ether. After recrystallizing once from 250 cm³ of dimethylformamide, 16 g of 3-ethoxycarbonyl-7,8-difluoro-1-methyl-4-oxo-1,4-dihydro-benzo[b][1,8]naphthyridine are obtained in the form of a yellow solid melting at 323°-324° C.

EXAMPLE 11

A solution, at about 2° C., of 14.6 g of ethylamine in 200 cm³ of ethanol is added in the course of 10 minutes, at between 2° and 5° C., with stirring, to a suspension of 20 g of ethyl 2-(2-chloro-6,7-difluoroquinoline-3-carbonyl)-3-dimethylaminoacrylate in 200 cm³ of ethanol at about 2° C., the mixture is stirred for a further 40 minutes at between 2° and 5° C. and the temperature is then allowed to rise to about 20° C. in the course of 2 hours. After 24 hours at about 20° C., the insoluble matter is drained and washed with 2 times 30 cm³ of ethanol and 2 times 50 cm³ of diisopropyl ether. 16.35 g of 3-ethoxycarbonyl-1-ethyl-7,8-difluoro-4-oxo-1,4-dihydrobenzo[b][1,8]naphthridine are obtained in the form of a beige solid melting at 290° C.

EXAMPLE 12

A solution, at about 5° C., of 10 g of methylamine in 50 cm³ of ethanol is added in the course of 10 minutes, at between 5° and 10° C., to a stirred suspension of 19.3 g of ethyl 2-(2-chloro-6,7,8-trifluoroquinoline-3-carbonyl)-3-dimethylaminoacrylate in 150 cm³ of ethanol kept at a temperature close to 5° C., the mixture is stirred for 1 hour at between 5° and 10° C. and the temperature is allowed to rise to about 20° C. 7.6 g of DBU are added to the solution obtained and the mixture is heated at about 30° C. for 1 hour. After cooling to a temperature close to 20° C., the product is drained and washed with twice 100 cm³ of ethanol and twice 100 cm³ of diisopropyl ether. 13.4 g of 3-ethoxycarbonyl-7,8,9-trifluoro-1-methyl-4-oxo-1,4-dihydro-benzo[b][1,8]naphthyridine are obtained in the form of a yellow solid melting at 320° C., which is used for the subsequent steps without further purification.

The ethyl 2-(2-chloro-6,7,8-trifluoroquinoline-3-carbonyl)-3-dimethylaminoacrylate can be prepared in the following manner:

A suspension of 26.7 g of ethyl 3-(2-chloro-6,7,8-trifluoro-3-quinolyl)-3-oxopropionate in 270 cm³ of ethyl acetate and 32 cm³ of N,N-dimethylformamide dimethyl acetal is heated at a temperature close to 75° C., with stirring, for 2 hours. The reaction mixture is concentrated to dryness under reduced pressure (20 kPa) at about 50° C. The dry extract is taken up in 175 cm³ of diisopropyl ether, drained and washed with twice 85 cm³ of the same solvent. 19.32 g of ethyl 2-(2-chloro-6,7,8-trifluoro quinoline-3-carbonyl)-3-dimethylaminoacrylate are obtained in the form of an orange solid melting at 118° C., which is used for the subsequent steps without further purification.

The ethyl 3-(2-chloro-6,7,8-trifluoro-3-quinolyl)-3-oxopropionate is prepared in the following manner:

A suspension of 46.3 g of 2-chloro-6,7,8-trifluoroquinoline-3-carboxylic acid in 640 cm³ of trichloromethane and 84 cm³ of thionyl chloride is heated, with stirring, at a temperature close to 60° C. for 6 hours. The solution obtained is concentrated to dryness under reduced pressure (20 kPa) at about 50° C. The dry extract obtained is taken up in 140 cm³ of petroleum ether (40–60), drained and washed with twice 60 cm³ of the same solvent. The 47.61 g of yellow solid obtained are brought into solution in 400 cm³ of tetrahydrofuran. This solution is introduced dropwise, with stirring, in the course of 1 hour and a half, at between 5° and 10 C., into 250 cm³ of a solution of the magnesium chelate of ethyl monomalonate in tetrahydrofuran prepared under the conditions of Example 8. The temperature is allowed to rise to about 20° C. and the mixture is stirred for a further 2 hours under these conditions. The solution obtained is introduced dropwise, with vigorous stirring, in the course of 1 hour, at a temperature close to 5° C., into 1750 cm³ of 0.5 N sulphuric acid. The mixture is stirred for a further 2 hours at this temperature and extracted at about 5° C. with 3 times 600 cm³ of diethyl ether. The combined organic phases are washed with 3 times 500 cm³ of water, dried over magnesium sulphate and concentrated under reduced pressure (20 kPa) at a temperature close to 30° C. The dry extract is taken up in a mixture of 135 cm³ of diisopropyl ether and 15 cm³ of n-hexane, drained at about 5° C. and washed with twice 115 cm³ of the same mixture at the same temperature. 47.4 g of ethyl 3-(2-chloro-6,7,8-trifluoro-3-quinolyl)-3-oxopropionate are obtained in the form of a beige solid melting at 78°–80° C., which is used for the subsequent steps without further purification.

The 2-chloro-6,7,8-trifluoroquinoline-3-carboxylic acid is prepared in the following manner:

A solution of 69.65 g of potassium permanganate in 730 cm³ of water is added in the course of 1 hour, while keeping the temperature between 10° and 14° C., to a stirred suspension, cooled to about 10° C., of 45.7 g of 2-chloro-6,7,8-trifluoro-3-formyl-1,4-dihydroquinoline in 585 cm³ of N potassium hydroxide solution. The mixture is stirred for a further 30 minutes at about 10° C. 12 g of sodium dithionite are added and the mixture is stirred for 10 minutes at a temperature close to 10° C. and filtered through diatomaceous silica and the filter cake is washed with 3 times 400 cm³ of water. The filtrate and the washings are combined and 70 cm³ of a 35% aqueous solution of hydrochloric acid are added. The precipitate formed is extracted with 3 times 500 cm³ of ethyl acetate. The combined organic extracts are dried over magnesium sulphate, filtered and concentrated under reduced pressure (20 kPa) at 50° C. The residue is taken up in a mixture of 100 cm³ of diethyl ether and 100 cm³ of diisopropyl ether, drained and washed with 100 cm³ of the same mixture. 46.43 g of 2-chloro-6,7,8-trifluoroquinoline-3-carboxylic acid are obtained in the form of a colourless solid which decomposes at 225°–230° C. and which is used for the subsequent steps without further purification.

The 2-chloro-6,7,8-trifluoro-3-formyl-1,4-dihydroquinoline is prepared in the following manner:

50 cm³ of phosphoryl chloride are added in the course of 40 minutes, with stirring, at between 5° and 10° C., to a mixture of 525 cm³ of trichloromethane and 49 cm³ of dimethylformamide, the mixture is stirred for 15 minutes at this temperature and the temperature is allowed to rise to about 20° C. 46.8 g of 6,7,8-trifluoro-3,4-dihydrocarbostyril are added progressively in the course of 20 minutes, at about 20° C., with vigorous stirring, to the solution obtained. The mixture is stirred for 30 minutes at a temperature close to 20° C., heated to about 60° C. and kept at this temperature for 2 hours and a half. The reaction mixture is concentrated under reduced pressure (20 kPa) at about 50° C. The oily residue is poured into 500 g of ice, with vigorous stirring. 100 g of sodium acetate are added in small fractions in the course of 30 minutes. The suspension obtained is poured in the course of 15 minutes, with vigorous stirring, into 1 liter of water which has previously been heated to about 90° C. and the mixture is stirred for a further 15 minutes at this temperature. The insoluble matter is drained at about 90° C. and washed with 3 times 250 cm³ of water. 47.7 g of 2-chloro-6,7,8-trifluoro-3-formyl-1,4-dihydroquinoline are obtained in the form of a colourless solid which decomposes at 220° C.

The 6,7,8-trifluoro-3,4-dihydrocarbostyril is prepared in the following manner:

24.35 g of 6,7,8-trifluorocarbostyril in suspension in a mixture of 450 cm³ of ethanol and 150 cm³ of dimethylformamide are hydrogenated, with stirring, at about 50° C., in the presence of 5 g of Raney nickel under a pressure of 1 atmosphere until the absorption of hydrogen has ceased. The W-2 grade Raney nickel used is washed beforehand with 50 cm³ of an aqueous 2% acetic acid solution, twice 50 cm³ of water and 3 times 50 cm³ of ethanol. 250 cm³ of dimethylformamide are added to the reaction mixture and the mixture is filtered at about 50 C. through diatomaceous silica. The filtrate is concentrated under reduced pressure (20 kPa) at about 70° C. The dry extract is taken up in 150 cm³ of water, drained and washed with twice 50 cm³ of water. 23.6 g of 6,7,8-trifluoro-3,4-dihydrocarbostyril are obtained in the form of a light beige solid melting at 217° C., which is used for the subsequent steps without further purification.

The 6,7,8-trifluorocarbostyril is prepared in the following manner:

60.83 g of 4-chloro-6,7,8-trifluorocarbostyril in suspension in 520 cm³ of acetic acid and 38.15 cm³ of triethylamine are hydrogenated under a pressure of 1 atmosphere in the presence of 5.25 g of 10% palladium-on-charcoal until the absorption of hydrogen has ceased, at a temperature close to 25° C. The reaction mixture is then heated to about 40° C. and filtered at this temperature through diatomaceous silica for filtration. The filtrate is concentrated under reduced pressure (20 kPa) at a temperature close to 50° C. The dry extract is taken up in 400 cm³ of water; the insoluble matter is drained and washed with 4 times 170 cm³ of water, twice 110 cm³ of ethanol and twice 100 cm³ of diisopropyl ether. 48.35 g of 6,7,8-trifluorocarbostyril are obtained in the form of a colourless solid which sublimes at 288° C. and which is used for the subsequent steps without further purification.

The 4-chloro-6,7,8-trifluorocarbostyril is prepared in the following manner:

A suspension of 70.4 g of 4-chloro-2-ethoxy-6,7,8-trifluoroquinoline in 170 cm³ of a 35% aqueous solution of hydrochloric acid, 420 cm³ of acetic acid and 250 cm³ of water is heated, with stirring, at a temperature close to 100° C. for 2 hours and a half. After cooling to about 20° C., the reaction mixture is poured into 1,100 cm³ of water at about 5° C., the mixture is stirred for 15 minutes at this temperature and the insoluble matter is then drained and washed with 3 times 220 cm³ of water. 61 g of 4-chloro-6,7,8-trifluorocarbostyril are obtained in the form of a cream solid melting at 213° C., which is used for the subsequent steps without further purification.

The 4-chloro-2-ethoxy-6,7,8-trifluoroquinoline is prepared in the following manner:

A suspension of 69.5 g of 2-ethoxy-6,7,8-trifluoro-4-hydroxyquinoline in 430 cm³ of phosphoryl chloride is heated, with stirring, at a temperature close to 100° C. for 30 minutes. The solution obtained is concentrated under reduced pressure (20 kPa) at about 60° C. until the volume is 100 cm³. The residue is taken up in 750 cm³ of ethyl acetate; the solution obtained is poured, with stirring, in the course of 10 minutes into a mixture of 400 cm³ of water and 200 g of ice and the mixture is stirred under these conditions for 30 minutes. After separating off the organic extract, the aqueous phase is extracted again with twice 250 cm³ of ethyl acetate. The combined organic extracts are washed with 3 times 250 cm³ of water, dried over magnesium sulphate and concentrated under reduced pressure (20 kPa) at about 40° C. The oily residue obtained is taken up in 370 cm³ of petroleum ether (40–60). After filtering through diatomaceous silica, the filtrate is concentrated to dryness under reduced pressure (20 kPa) at about 30° C. 70.7 g of 4-chloro-2-ethoxy-6,7,8-trifluoroquinoline are obtained in the form of a beige solid melting at 45° C., which is used for the subsequent steps without further purification.

The 2-ethoxy-6,7,8-trifluoro-4-hydroxyquinoline can be prepared in the following manner:

A solution of 122 g of 2,3,4-trifluoro-N-[(1'-ethoxy-2'-ethoxycarbonyl)ethylidene]-aniline in 120 cm³ of phenyl oxide is introduced dropwise, in the course of 25 minutes, with stirring, into 600 cm³ of phenyl oxide at a temperature close to 250° C. while removing the ethanol formed by distillation. After stirring for 15 minutes at this temperature, the solution is cooled to about 20° C. and 750 cm³ of n-hexane are added. The precipitate formed is drained and washed 3 times with 200 cm³ of n-hexane. 69.5 g of 2-ethoxy-6,7,8-trifluoro-4-hydroxyquinoline are obtained in the form of a beige solid melting at 171° C., which is used for the subsequent steps without further purification.

The 2,3,4-trifluoro-N-[(1'-ethoxy-2'-ethoxycarbonyl)ethylidene]-aniline can be prepared in the following manner:

58.8 g of 2,3,4-trifluoroaniline are added in a single amount, with stirring, to a solution of 90 g of 2-ethoxycarbonyl-1-ethoxy-ethylideneamine hydrochloride in 820 cm³ of ethanol. After stirring for 48 hours at a temperature close to 20° C., the suspension obtained is filtered; the filtrate is concentrated under reduced pressure (20 kPa) at a temperature close to 50° C. The oily residue is taken up in 250 cm³ of water. The mixture obtained is extracted with 3 times 200 cm³ of diethyl ether. The combined organic extracts are washed with 4 times 150 cm³ of water, dried over magnesium sulphate and concentrated under reduced pressure (20 kPa) at about 30° C. 122 g of 2,3,4-trifluoro-N-[(1'-ethoxy-2'-ethoxycarbonyl)ethylidene ]-aniline are obtained in the form of a yellow oil which is used for the subsequent steps without further purification.

The 2-ethoxycarbonyl-1-ethoxy-ethylideneamine hydrochloride was prepared by the method described by A. Pinner, et al., Ber. Dtsch. Chem. Ges., 28, 478 (1895).

EXAMPLE 13

4.5 g of ethylamine are added in the course of 10 minutes, at between 5° and 10° C., to a stirred suspension of 7.1 g of ethyl 2-(2-chloro-6,7,8-trifluoroquinoline-3-carbonyl)-3-dimethylaminoacrylate in 100 cm³ of ethanol kept at a temperature close to 5° C., the mixture is stirred for 1 hour at between 5° and 10° C. and the temperature is allowed to rise to about 20° C. 4 g of 1,8-diazabicyclo[5.4.0]undec-7-ene (DBU) are added to the solution obtained and the mixture is heated at a temperature close to 75° C. for 1 hour and a half. After cooling to a temperature close to 20° C., the product is drained and washed with twice 30 cm³ of ethanol and twice 50 cm³ of diisopropyl ether. 4 g of 3-ethoxycarbonyl-1-ethyl-7,8,9-tri fluoro-4-oxo-1,4-dihydro-benzo[b][1,8]naphthyridine are obtained in the form of a cream solid melting at 284° C., which is used for the subsequent steps without further purification.

EXAMPLE 14

9.5 g of tert.-butylamine are added at a temperature of about 20° C., in the course of 5 minutes, to a stirred solution of 11.7 g of ethyl 2-(2-chloro-6,7,8-trifluoroquinoline-3-carbonyl)-3-dimethylaminoacrylate in 150 cm³ of trichloromethane at the same temperature. After stirring for 4 hours at about 20° C., the solution is concentrated to dryness under reduced pressure (20 kPa) at about 50° C. The residue obtained is taken up in 100 cm³ of ethanol. 5 g of DBU are added to the solution obtained and the mixture is heated at a temperature close to 75° C. for 3 hours. After cooling to about 20° C., the precipitate obtained is drained and washed with twice 50 cm³ of ethanol and twice 50 cm³ of diisopropyl ether. 9.5 g of 3-ethoxycarbonyl-7,8,9-trifluoro-4-oxo-1-tert.-butyl-1,4-dihydro-benzo[b][1,8]naphthyridine are obtained in the form of a colourless solid melting at 229° C., which can be used for the subsequent steps without further purification.

EXAMPLE 15

4.12 g of cyclopropylamine are added in the course of 5 minutes to a solution of 7 g of ethyl 2-(2-chloro-6,7,8-trifluoroquinoline-3-carb onyl)-3-dimethylamino-acrylate in 100 cm³ of trichloromethane kept at a temperature close to 20° C. and the mixture is stirred for a further 4 hours at this temperature. The reaction mixture is concentrated under reduced pressure (20 kPa) at about 50° C. The oily residue obtained is taken up in 100 cm³ of ethanol and 3 g of DBU. The mixture is heated to 80° C. and kept at this temperature, with stirring, for 1 hour and a half. After cooling to about 20° C., the insoluble matter is drained and washed with twice 30 cm³ of ethanol and twice 30 cm³ of diisopropyl ether. 4.5 g of 1-cyclopropyl-3-ethoxycarbonyl-7,8,9-trifluoro-4-oxo-1,4-dihydro-benzo[b][1,8]naphthridine are obtained in the form of a colourless solid melting at 260° C.

EXAMPLE 16

8.7 cm³ of triethylamine are added to a suspension of 5.1 g of methylhydroxylamine hydrochloride in 120 cm³ of trichloromethane. 7.8 g of ethyl 2-(2-chloro-6,7,8-trifluoroquinoline-3-carbonyl)-3-dimethylaminoacrylate are added, at about 20° C., to the solution obtained. After stirring for 2 hours at this temperature, the solution is concentrated to dryness under reduced pressure (20 kPa) at about 50° C. The residue obtained is taken up in 150 cm³ of ethanol and 10 cm³ of triethylamine and the mixture is heated, with stirring, for 30 minutes. After cooling to about 20° C., the insoluble matter is drained and washed with 3 times 50 cm³ of ethanol and twice 50 cm³ of diisopropyl ether. After recrystallizing from 120 cm³ of dimethylformamide, 9 g of 3-ethoxycarbonyl-6,7,8-trifluoro-1-methoxy-4-oxo-1,4-dihydro-benzo[b][1,8]naphthyridine are obtained in the form of a yellow solid melting at 298°-300° C.

The products according to the invention can be used in the following manner:

REFERENCE EXAMPLE 1

A suspension of 15 g of 8-chloro-3-ethoxycarbonyl-7-fluoro-1-methyl-4-oxo-1,4-dihydro-benzo[b][1,8]naphthyridine in 150 cm³ of acetic acid and 150 cm³ of hydrochloric acid as a 17.5% aqueous solution is heated at a temperature close to 100° C., with stirring, for 4 hours. After cooling to a temperature close to 20° C., the product is drained and washed with twice 150 cm³ of ethanol and then twice 100 cm³ of diethyl ether. 12.7 g of 8-chloro-7-fluoro-1-methyl-4-oxo-1,4-dihydro-benzo[b][1,8]naphthyridine-3-carboxylic acid are obtained in the form of a beige solid which sublimes at 400°-405° C. and is used for the subsequent steps without further purification.

A suspension of 3.5 g of 8-chloro-7-fluoro-1-methyl-4-oxo-1,4-dihydro-benzo[b][1,8]naphthyridine-3-carboxylic acid and 4.6 g of 2-methylpiperazine in 40 cm³ of pyridine is heated at a temperature close to 115° C., with stirring, for 13 hours. The reaction mixture is concentrated to dryness under reduced pressure (20 kPa) at 60° C. The residue is twice taken up with 30 cm³ of ethanol and concentrated under reduced pressure under the above conditions. The solid obtained is taken up in 60 cm³ of water and 10 cm³ of 30% aqueous potassium hydroxide solution. The aqueous phase is washed with twice 100 cm³ of trichloromethane, 10.28 g of methanesulphonic acid are added and the aqueous phase is again washed with twice 100 cm³ of trichloromethane. 10 cm³ of 30% aqueous potassium hydroxide solution are added. The precipitate formed is drained and washed with 3 times 10 cm³ of water and twice 10 cm³ of ethanol. 2.7 g of 7-fluoro-1-methyl-8-(3-methyl-1-piperazinyl)-4-oxo-1,4-dihydro-benzo[b][1,8]naphthyridine-3-carboxylic acid are obtained in the form of a yellow solid melting at 360°-363° C.

REFERENCE EXAMPLE 2

Carrying out the reaction under the conditions of Reference Example 1 but, starting from 10 g of 8-chloro-7-fluoro-1-methyl-4-oxo-1,4-dihydro-benzo[b][1,8]naphthyridine-3-carboxylic acid and 28 g of piperazine in 100 cm³ of pyridine, 5.5 g of 7-fluoro-1-methyl-4-oxo-8-(1-piperazinyl)-1,4-dihydro-benzo[b][1,8]naphthyridine-3-carboxylic acid hemihydrate are obtained in the form of a yellow solid melting at 370°-375° C.

REFERENCE EXAMPLE 3

The reaction is carried out under conditions analogous to Reference Example 1 but starting from 5 g of 8-chloro-7-fluoro-1-methyl-4-oxo-1,4-dihydro-benzo[b][1,8]naphthyridine-3-carboxylic acid and 16 g of 1-methylpiperazine in 50 cm³ of pyridine. After concentrating the reaction mixture under reduced pressure, 25 cm³ of acetic acid are added to the residue, which is suspended in 100 cm³ of water. A very small amount of insoluble matter is removed by filtration through diatomaceous silica for filtration. 200 cm³ of 3 N aqueous potassium hydroxide solution are added to the filtrate and a very small amount of insoluble matter is again removed by filtration through diatomaceous silica for filtration. 5 cm³ of acetic acid are added to the filtrate. The precipitate formed is drained and washed with 3 times 50 cm³ of water. After recrystallizing twice from 17 cm³ of dimethylformamide each time, 3.2 g of 7-fluoro-I-methyl-8-(4-methyl-1-piperazinyl)-4-oxo-1,4-di hydro-benzo[b][1,8]-naphthyridine-3-carboxylic acid are obtained in the form of a yellow solid melting at 356° C.

REFERENCE EXAMPLE 4

Carrying out the reaction under the conditions described below in Reference Example 5, but starting from 1.85 g of 8-chloro-7-fluoro-1-methyl-4-oxo-1,4-dihydro-benzo[b][1,8]naphthyridine-3-carboxylic acid and 2.75 g of 1-ethylpiperazine in 20 cm³ of pyridine, 1.3 g of 8-(4-ethyl-1-piperazinyl)-7-fluoro-1-methyl-4-oxo-1,4-dihydro-benzo[b][1,8]naphthyridine-3-carboxylic acid are obtained in the form of a yellow solid melting at 285°-286° C.

REFERENCE EXAMPLE 5

The reaction is carried out under the conditions of Reference Example 1 but starting from 1.6 g of 8-chloro-7-fluoro-1-methyl-4-oxo-1,4-dihydro-benzo[b][1,8]naphthyridine-3-carboxylic acid and 6.8 g of 1-(2-hydroxyethyl)-piperazine in 16 cm³ of pyridine. After concentrating the reaction mixture to dryness under reduced pressure, the residue is taken up in 50 cm³ of water. The mixture is brought to pH 6.9 by adding 0.4 cm³ of acetic acid. The precipitate obtained is drained, washed with twice 10 cm³ of water and recrystallized twice from 10 cm³ of dimethylformamide. 1.1 g of 7-fluoro-8-[4-(2-hydroxyethyl)-1-piperazinyl]-1-methyl-4-oxo-1,4-di hydro-benzo[b][1,8]naphthyridine-3-carboxylic acid are obtained in the form of a yellow solid melting at 275°-276° C.

REFERENCE EXAMPLE 6

The reaction is carried out under the conditions of Reference Example 3 but starting from 1.7 g of 8-chloro-7-fluoro-1-methyl-4-oxo-1,4-dihydro-benzo[b][1,8]naphthyridine-3-carboxylic acid and 2.5 g of 2,6-dimethylpiperazine in 20 cm³ of pyridine. 1.1 g of 8-(3,5-dimethyl-1-piperazinyl)-7-fluoro-1-methyl-4-oxo-1,4-dihydro-benzo[b][1,8]naphthyridine-3-carboxylic acid hemihydrate are obtained in the form of a yellow solid melting at 294°-295° C.

REFERENCE EXAMPLE 7

Carrying out the reaction under the conditions of Reference Example 1, but starting from 10.5 g of 8-chloro-7-fluoro-3-ethoxycarbonyl-1-ethyl-4-oxo-1,4-dihydro-benzo[b][1,8]naphthyridine, 9.3 g of 8-chloro-1-ethyl-7-fluoro-4-oxo-1,4-dihydro-benzo[b]1,8]-naphthyridine-3-carboxylic acid are obtained in the form of a beige solid melting at 380° C., which is used for the subsequent steps without further purification.

1-Ethyl-7-fluoro-8-(1-piperazinyl)-4-oxo-1,4-dihydro-benzo[b][1,8]naphthyridine-3-carboxylic acid is prepared under the conditions of Reference Example 5, but starting from 1.6 g of 8-chloro-1-ethyl-7-fluoro-4-oxo- 1,4-dihydro-benzo[b][1,8]naphthyridine-3-carboxylic acid and 4.3 g of piperazine in 20 cm³ of pyridine. After recrystallizing 3 times from, in total, 300 cm³ of dimethylformamide, 0.94 g of 1-ethyl-7-fluoro-8-(1-piperazinyl)-4-oxo-1,4-dihydro-benzo[b][1,8]-naphthyridine-3-carboxylic acid trihydrate is obtained in the form of a yellow solid melting at 320°–322° C.

REFERENCE EXAMPLE 8

The reaction is carried out under the conditions of Reference Example 5 but starting from 1.6 g of 8-chloro-1-ethyl-7-fluoro-4-oxo-1,4-dihydro-benzo[b][1,8]naphthyridine-3-carboxylic acid and 4.5 g of 4-methylpiperazine in 16 cm³ of pyridine. After recrystallizing 4 times from, in total, 120 cm³ of dimethylformamide, 1.2 g of 1-ethyl-7-fluoro-8-(4-methyl-1-piperazinyl)-4-oxo-1,4-dihydro-benzo[b][1,8]naphthyridine-3-carboxylic acid are obtained in the form of a yellow solid melting at 285°–286° C. solvated with 1% of water.

REFERENCE EXAMPLE 9

The reaction is carried out under the conditions of Reference Example 1 but starting from 2.1 g of 8-chloro-1-ethyl-7-fluoro-4-oxo-1,4-dihydro-benzo[b][1,8]naphthyridine-3-carboxylic acid, 20 cm³ of pyridine and 2.4 g of 2-methylpiperazine. After taking up in ethanol and concentrating to dryness under reduced pressure (20 kPa at 50° C.), the solid residue is taken up in 20 cm³ of water and 10 cm³ of 2 N potassium hydroxide solution The aqueous solution obtained is washed with twice 20 cm³ of trichloromethane, 10 cm³ of acetic acid are added and the mixture is again washed with twice 40 cm³ of trichloromethane. 23 cm³ of 4.5 N potassium hydroxide solution are added and the suspension obtained is heated to a temperature close to 90° C. After cooling to a temperature close to 20° ., the 90° C. After cooling to a temperature close to 20° C., the precipitate is drained and washed with 3 times 10 cm³ of water and twice 10 cm³ of ethanol. After recrystallizing twice from 120 cm³ of dimethylformamide each time, 1.7 g of 1-ethyl-7-fluoro-8-(3-methyl-1-piperazinyl)-4-oxo-1,4-dihydro-benzo[b][1,8]naphthyridine-3-carboxylic acid are obtained in the form of a yellow solid melting at 310°–312° C.

REFERENCE EXAMPLE 10

Carrying out the reaction under the conditions of Reference Example 5, but starting from 1.6 g of 8- chloro-1-ethyl-7-fluoro-4-oxo-1,4-dihydro-benzo[b][1,8-]naphthyridine-3-carboxylic acid and 2.3 g of 1-ethylpiperazine in 16 cm³ of pyridine, 1.4 g of 1-ethyl-8-(4-ethyl-1-piperazinyl)-7-fluoro-4-oxo-1,4-dihydro-benzo[b][1,8]naphthyridine-3-carboxylic acid are obtained in the form of a yellow solid melting at 287°–288° C., solvated by 1.6% of water.

REFERENCE EXAMPLE 11

Carrying out the reaction under the conditions of Reference Example 5, but starting from 1.6 g of 8-chloro-1-ethyl-7-fluoro-4-oxo-1,4-dihydro-benzo[b][1,8]naphthyridine-3-carboxylic acid and 2.6 g of 1-(2-hydroxyethyl)-piperazine in 16 cm³ of pyridine, 1.3 g of 1-ethyl-7-fluoro-8-[4-(2-hydroxyethyl)-1-piperazinyl]-4-oxo-1,4-dihydro-benzo[b][1,8]naphthyridine-3-carboxylic acid are obtained in the form of a yellow solid melting at 264°–265° C.

REFERENCE EXAMPLE 12

A suspension of 16.4 g of 8-chloro-3-ethoxycarbonyl-7-fluoro-1-(N-formyl-N-methylamino)-4-oxo-1,4-dihydro-benzo[b][1,8]naphthyridine in 164 cm³ of acetic acid and 164 cm³ of an aqueous 17.5% hydrochloric acid solution is heated at a temperature close to 100° C., with stirring, for 4 hours. After cooling to a temperature close to 10° C., 165 cm³ of 30% slate lime is added at between 10° and 20° C. The product is drained and washed with 3 times 150 cm³ of water, 3 times 150 cm³ of ethanol and 3 times 150 cm³ of diethyl ether. 13.64 g of 8-chloro-7-fluoro-1-methylamino-4-oxo-1,4-dihydro-benzo[b][1,8]naphthyridine-3-carboxylic acid are obtained in the form of a yellow solid melting at 354°–356° C., which is used for the subsequent steps without further purification.

7-Fluoro-1-methylamino-4-oxo-8-(1-piperazinyl)-1,4-dihydro-benzo[b][1,8]naphthyridine-3-carboxylic acid is prepared under the conditions of Reference Example 5 but starting from 2.25 g of 8-chloro-7-fluoro-1-methylamino-4-oxo-1,4-dihydro-benzo[b][1,8]-naphthyridine-3-carboxylic acid and 2.4 g of piperazine in 30 cm³ of pyridine. After recrystallizing 3 times from, in total, 400 cm³ of dimethylformamide, 0.82 g of 7-fluoro-1-methylamino-4-oxo-8-(1-piperazinyl)-1,4-dihydro-benzo[b][1,8]naphthyridine-3-carboxylic acid is obtained in the form of a deep yellow solid melting at 322°–324° C., solvated by 13.6% of dimethylformamide.

REFERENCE EXAMPLE 13

The reaction is carried out under the conditions of Reference Example 1 but starting from 1.93 g of 8-chloro-7-fluoro-1-methylamino-4-oxo-1,4-dihydro-benzo[b][1,8]naphthyridine-3-carboxylic acid, 2.4 g of 1-methylpiperazine and 20 cm³ of pyridine. After recrystallizing twice from 15 cm³ of dimethylformamide each time, 0.9 g of 7-fluoro-1-methylamino-8-(4-methyl-1-piperazinyl)-4-oxo-1,4-dihydro-benzo[b][1,8]-naphthyridine-3-carboxylic acid is obtained in the form of a yellow solid melting at 263°–264° C.

REFERENCE EXAMPLE 14

The reaction is carried out under the conditions of Reference Example 5 but starting from 3.2 g of 8-chloro-7-fluoro-1-methylamino-4-oxo-1,4-dihydro-benzo[b][1,8]naphthyridine-3-carboxylic acid and 4 g of 2-methylpiperazine in 40 cm³ of pyridine. The crude product obtained is taken up in 30 cm³ of water and 7 cm³ of 2 N aqueous potassium hydroxide solution. A very small amount of insoluble matter is removed by filtration through diatomaceous silica. The filtrate is washed with twice 20 cm³ of diethyl ether and the product is then precipitated by adding 3.5 cm³ of 4 N methanesulphonic acid. The precipitate obtained is drained and washed with 3 times 20 cm³ of water and 3 times 20 cm³ of ethanol 2.2 g of 7-fluoro-1-methylamino-8-(3-methyl-1-piperazinyl)-4-oxo-1,4-dihydro-benzo[b][1,8-]naphthyridine-3-carboxylic acid are obtained in the form of a deep yellow solid melting at 343°–345° C., solvated by 3.7% of water.

REFERENCE EXAMPLE 15

Carrying out the reaction under the conditions of Reference Example 1, but starting from 6.1 g of 8-chloro-1-cyclopropyl-3-ethoxycarbonyl-7-fluoro-4-oxo-1,4-dihydro-benzo[b][1,8]naphthyridine, 4.85 g of 8-chloro-1-cyclopropyl-7-fluoro-4-oxo-1,4-dihydrobenzo[b][1,8]naphthyridine-3-carboxylic acid are obtained in the form of a yellow solid melting at 330° C., which is used for the subsequent steps without further purification.

1-Cyclopropyl-7-fluoro-4-oxo-8-(1-piperazinyl)-1,4-dihydro-benzo[b][1,8]naphthyridine-3-carboxylic acid is prepared under the conditions of Reference Example 5 but starting from 1 g of 8-chloro-1-cyclopropyl-7-fluoro-4-oxo-1,4-dihydro-benzo[b][1,8]naphthyridine-3-carboxylic acid and 2.6 g of piperazine in 10 cm$^3$ of pyridine, 0.6 g of 1-cyclopropyl-7-fluoro-4-oxo-8-(1-piperazinyl)-1,4-dihydro-benzo[b][1,8]naphthyridine-3-carboxylic acid dihydrate is obtained in the form of a yellow solid melting at 342°-343° C.

REFERENCE EXAMPLE 16

The reaction is carried out under the conditions of Reference Example 5 but starting from 1 g of 8-chloro-1-cyclopropyl-7-fluoro-4-oxo-1,4-dihydro-benzo[b][1,8-]naphthyridine-3-carboxylic acid and 3 g of 1-methyl-piperazine in 10 cm$^3$ of pyridine. After recrystallizing from 10 cm$^3$ of dimethylformamide, 0.63 g of 1-cyclopropyl-7-fluoro-8-(4-methyl-1-piperazinyl)-4-oxo-1,4-dihydro-benzo[b][1,8]naphthyridine-3-carboxylic acid is obtained in the form of a yellow solid melting at 250° C.

REFERENCE EXAMPLE 17

The reaction is carried out under the conditions of Reference Example 1 but starting from 1 g of 8-chloro-1-cyclopropyl-7-fluoro-4-oxo-1,4-dihydro-benzo[b][1,8-]naphthyridine-3-carboxylic acid and 3 g of 2-methyl-piperazine in 10 cm$^3$ of pyridine. The pure product is obtained after a supplementary purification by recrystallization from 200 cm$^3$ of dimethylformamide. 0.5 g of 1-cyclopropyl-7-fluoro-8-(3-methyl-1-piperazinyl)-4-oxo-1,4-dihydro-benzo[b][1,8]-naphthyridine-3-carboxylic acid hemihydrate is obtained in the form of a yellow solid melting at 343° C.

REFERENCE EXAMPLE 18

The reaction is carried out under the conditions of Reference Example 5 but starting from 2 g of 8-chloro-1-cyclopropyl-7-fluoro-4-oxo-1,4-dihydro-benzo[b][1,8-]naphthyridine-3-carboxylic acid and 2.74 g of 1-ethyl-piperazine in 20 cm, of pyridine. The pure product is isolated after a first recrystallization from 105 cm$^3$ of ethanol containing 25% of dimethylformamide followed by a second recrystallization from 75 cm$^3$ of ethanol containing 50% of dimethylformamide. 0.67 g of 1-cyclopropyl-8-(4-ethyl-1-piperazinyl)-7-fluoro-4-oxo-1,4-dihydro-benzo[b][1,8]naphthyridine-3-carboxylic acid is obtained in the form of a yellow-green solid melting at 254° C.

REFERENCE EXAMPLE 19

The reaction is carried out under conditions analogous to Reference Example 5 but starting from 4 g of 8-chloro-1-cyclopropyl-7-fluoro-4-oxo-1,4-dihydro-benzo[b][1,8]naphthyridine-3-carboxylic acid and 6.2 g of 1-(2-hydroxyethyl)-piperazine in 40 cm$^3$ of pyridine The reaction mixture is heated for 22 hours at a temperature close to 115° C. The pure product is isolated after recrystallizing 3 times from 3 times 200 cm$^3$ of ethanol containing 10% of dimethylformamide each time. 0.94 g of 1-cyclopropyl-7-fluoro-8-[4-(2-hydroxyethyl)-1-piperazinyl]-4-oxo-1,4-dihydro-benzo[b][1,8]naphthyridine-3-carboxylic acid is obtained in the form of a yellow solid melting at 255° C.

REFERENCE EXAMPLE 20

A suspension of 1.88 g of 8-chloro-3-ethoxy-carbonyl-7-fluoro-4-oxo-1-tert.-butyl-1,4-dihydro-benzo[b][1,8]naphthyridine in 10 cm$^3$ of ethanol, 5 cm$^3$ of water and 15 cm$^3$ of 2 N aqueous potassium hydroxide solution is heated at a temperature close to 75° C., with stirring, for one hour. 2 cm$^3$ of acetic acid are added to the solution obtained. The precipitate formed is drained and washed with 3 times 10 cm$^3$ of water and 3 times 10 cm$^3$ of ethanol. After recrystallizing from 50 cm$^3$ of dimethylformamide, 1.7 g of 8-chloro-7-fluoro-4-oxo-1-tert.-butyl-1,4-dihydro-benzo[b][1,8]-naphthyridine-3-carboxylic acid are obtained in the form of a yellow solid melting at 398° C.

The reaction is carried out under the conditions of Reference Example 5 but starting from 1.7 g of 8-chloro-7-fluoro-4-oxo-1-tert.-butyl-1,4-dihydro-benzo[b][1,8]naphthyridine-3-carboxylic acid and 4.3 g of piperazine in 20 cm$^3$ of pyridine. The pure product is obtained after a single recrystallization from 20 cm$^3$ of dimethylformamide. 1.25 g of 7-fluoro-4-oxo-8-(1-piperazinyl)-1-tert.-butyl-1,4-dihydro-benzo[b][1,8-]naphthyridine-3-carboxylic acid are isolated in the form of a yellow solid melting at 290° C., solvated by 4.5% of water.

REFERENCE EXAMPLE 21

A solution of 1.15 g of 7-fluoro-1-methyl-8-(3-methyl-1-piperazinyl)-4-oxo-1,4-dihydro-benzo[b][1,8]naphthyridine-3-carboxylic acid in 1.35 cm$^3$ of 98% formic acid and 3.25 cm$^3$ of a 30% aqueous formaldehyde solution is heated at a temperature close to 100° C. for 2 hours. The reaction mixture is concentrated under reduced pressure (20 kPa) at 50° C. and 5 cm$^3$ of water are then added, the solution obtained is brought to pH 7 by adding 0.5 cm$^3$ of 2 N aqueous potassium hydroxide solution and heated at a temperature close to 100° C. for 2 minutes. The product, which crystallizes, is drained at 20° C. and washed with twice 10 cm$^3$ of water. The crude product obtained is recrystallized twice from 10 cm$^3$ dimethylformamide each time. 0.55 g of 8-(3,4-dimethyl-1-piperazinyl)-7-fluoro-1-methyl-4-oxo-1,4-dihydro-benzo [b][1,8]-naphthyridine-3-carboxylic acid is obtained in the form of a yellow solid melting at 306°-308° C.

REFERENCE EXAMPLE 22

The reaction is carried out under the conditions of Reference Example 21, but starting from 2.3 g of 1-ethyl-7-fluoro-8-(3-methyl-1-piperazinyl)-4-oxo-1,4-dihydro-benzo[b][1,8]naphthyridine-3-carboxylic acid, 2.26 cm$^3$ of 98% formic acid and 5.6 cm$^3$ of a 30% aqueous solution of formaldehyde, 1.75 g of 8-(3,4-dimethyl-1-piperazinyl)-1-ethyl-7-fluoro-4-oxo-1,4-dihydro-benzo[b][1,8]naphthyridine-3-carboxylic acid are obtained in the form of a yellow solid melting at 293°-294° C.

REFERENCE EXAMPLE 23

The reaction is carried out under the conditions of Reference Example 21, but starting from 1.9 g of 1-cyclopropyl-7-fluoro-8-(3-methyl-1-piperazinyl)-4-oxo-1,4-dihydro-benzo[b][1,8]naphthyridine-3-carboxylic acid, 1.38 cm$^3$ of formic acid and 3.30 cm$^3$ of a 30% aqueous solution of formaldehyde. After recrystallizing the crude product from 50 cm³ of ethanol, 1.3 g of 1-cyclopropyl-8-(3,4-dimethyl-1-piperazinyl)-7-fluoro-4-oxo-1,4-dihydro-benzo[b][1,8]naphthyridine-3-carboxylic acid are obtained in the form of a yellow solid melting at 219° C.

REFERENCE EXAMPLE 24

The reaction is carried out under the conditions described below in Reference Example 30, but starting from 2.2 g of 8-chloro-3-ethoxycarbonyl-7-fluoro-1-(2-fluoroethyl)-4-oxo-1,4-dihydro-benzo[b][1,8]-naphthyridine. After recrystallizing twice from 10 cm³ of dimethylformamide each time, 1.4 g of 8-chloro-7-fluoro-1-(2-fluoroethyl)-4-oxo-1,4-dihydro-benzo[b][1,8]naphthyridine-3-carboxylic acid are obtained in the form of a yellow solid melting at 310° C.

A suspension of 1.2 g of 8-chloro-7-fluoro-1-(2-fluoroethyl)-4-oxo-1,4-dihydro-benzo[b][1,8]-naphthyridine-3-carboxylic acid in 12 cm³ of pyridine and 3.52 g of 1-methylpiperazine is heated, with stirring, at a temperature close to 110° C. for 6 hours. After treatment under the conditions described in Reference Example 3, 0.6 g of 7-fluoro-1-(2-fluoroethyl)-8-(4-methyl-1-piperazinyl)-4-oxo-1,4-dihydro-benzo[b][1,8]naphthrydine-3-carboxylic acid is obtained in the form of a yellow solid melting at 306°–308° C.

REFERENCE EXAMPLE 25

A suspension of 1.95 g of 1-cyclopropyl-3-ethoxycarbonyl-7,8-difluoro-4-oxo-1,4-dihydro-benzo[b][1,8-]naphthyridine in 20 cm³ of 17.5% hydrochloric acid and 20 cm³ of acetic acid is heated at a temperature close to 100° C. for 1 hour 30 minutes. After cooling to about 20° C., the reaction mixture is poured into 100 cm³ of water. The precipitate is drained and washed with 3 times 20 cm³ of water. After recrystallizing once from a mixture of 30 cm³ of dimethylformamdide and 30 cm³ of ethanol, 1.31 g of 1-cyclopropyl-7,8-difluoro-4-oxo-1,4-dihydro-benzo[b][1,8]naphthyridine-3-carboxylic acid are obtained in the form of a yellow solid melting at 284°–285° C.

A suspension of 0.47 g of 1-cyclopropyl-7,8-difluoro-4-oxo-1,4-dihydro-benzo[b][1,8]naphthyridine-3-carboxylic acid and 0.6 g of 1-methylpiperazine in 7 cm³ of dimethyl sulphoxide is heated at a temperature close to 80° C. for 15 minutes. The reaction mixture is poured into 25 cm³ of water and 9 cm³ of N hydrochloric acid are added. The solid obtained is drained and washed with 3 times 5 cm³ of water. After recrystallizing once from a mixture of 4.3 cm³ of ethanol and 4.5 cm³ of dimethylformamide, 0.29 g of 1-cyclopropyl-7-fluoro-8-(4-methyl-1-piperazinyl)-4-oxo-1,4-dihydro-benzo[b][1,8]naphthyridine-3-carboxylic acid is obtained in the form of a yellow solid melting at 250° C.

REFERENCE EXAMPLE 26

A suspension of 2.78 g of 3-ethoxycarbonyl-7,8-difluoro-1-methoxy-4-oxo-1,4-dihydro-benzo[b][1,8-]naphthyridine in 30 cm³ of 17.5% of hydrochloric acid and 30 cm, of acetic acid is heated at a temperature close to 100° C. for 1 hour. After cooling to about 20° C., the reaction mixture is poured into 100 cm³ of water. The precipitate formed is drained and washed with 3 times 30 cm³ of water and twice 5 cm³ of ethanol. After recrystallizing from 100 cm³ of dimethylformamide containing 20% of ethanol, 2.03 g of 7,8-difluoro-1-methoxy-4-oxo-1,4-dihydro-benzo[b][1,8]naphthyridine-3-carboxylic acid are obtained in the form of a yellow solid melting at 325°–327° C.

A suspension of 0.93 g of 7,8-difluoro-1-methoxy-4-oxo-1,4-dihydro-benzo[b][1,8]naphthyridine-3-carboxylic acid in 0.6 g of 1-methylpiperazine and 20 cm³ of dimethyl sulphoxide is heated at a temperature close to 80° C. for 5 minutes. After cooling to about 20° C., the reaction mixture is poured into 30 cm³ of water, 1.5 cm³ of 2 N methanesulphonic acid are added and the product is drained and washed with 3 times 5 cm³ of water. After recrystallizing from 30 cm³ of dimethylformamide containing 30% of ethanol, 0.55 g of 7-fluoro-1-methoxy-8-(4-methyl-1-piperazinyl)-4-oxo-1,4-dihydro-benzo[b][1,8]naphthyridine-3-carboxylic acid is obtained in the form of a brown solid melting at 270° C.

REFERENCE EXAMPLE 27

Carrying out the reaction as described above in Reference Example 2, 2 g of 7,8-difluoro-1-methoxy-4-oxo-1,4-dihydro-benzo[b][1,8]naphthyridine-3-carboxylic acid are prepared and are suspended in 2.8 g of piperazine and 40 cm³ of dimethyl sulphoxide and the mixture is stirred for 15 minutes at a temperature close to 40° C. After cooling to about 20° C. the reaction mixture is poured into 150 cm³ of water and 27.75 cm³ of 2N methanesulphonic acid are added. A very small amount of insoluble matter is removed by filtration through diatomaceous silica. 15 cm³ of 2N aqueous potassium hydroxide solution are added to the solution obtained. The precipitate formed is drained, washed with 3 times 15 cm³ of water and taken up in 100 cm³ of dimethylformamide and the mixture is heated, with stirring, for 10 minutes at a temperature close to 150° C. The suspension is cooled to about 100° C.; the insoluble matter is drained and taken up in 100 cm³ of ethanol and the mixture is heated at a temperature close to 75° C. for 1 hour. The insoluble matter is drained at about 50° C. and washed with 40 cm³ of the same solvent, at the same temperature as before 1.8 g of 7-fluoro-1-methoxy-4-oxo-8-(1-piperazinyl)-1,4-dihydro-benzo[b][1,8]naphthyridine-3-carboxylic acid are obtained in the form of a brown solid melting at 298°–300° C., which is solvated by 2.4% of water.

REFERENCE EXAMPLE 28

A suspension of 1.2 g of 1-cyclopropyl-3-ethoxycarbonyl-7,8-difluoro-4-oxo-1,4-dihydro-benzo[b][1,8-]naphthyridine in 1.4 g of 1-methylpiperazine and 20 cm³ of dimethyl sulphoxide is heated at a temperature close to 95° C. for 45 minutes. After cooling to a temperature close to 20° C., the reaction mixture is diluted with 100 cm³ of water and extracted with 3 times 30 cm³ of trichloromethane. The combined organic extracts are washed with 3 times 30 cm³ of water, dried over magnesium sulphate, filtered and concentrated under reduced pressure (20 kPa) at a temperature close to 50° C. The solid obtained is taken up in 20 cm³ of diisopropyl ether, drained, washed with 10 cm³ of the same solvent and recrystallized from 150 cm³ of ethyl acetate. 1.1 g of 1-cyclopropyl-3-ethoxycarbonyl-7-fluoro-8-(4-methyl-1-piperazinyl)-4-oxo-1,4-dihydro-benzo[b][1,8]naphthyridine are obtained in the form of a yellow solid melting at 223° C.

A suspension of 0.85 g of 1-cyclopropyl-7-fluoro-3-ethoxycarbonyl-8-(4-methyl-1-piperazinyl)-4-oxo-1,4-dihydro-benzo[b][1,8]naphthyridine in 12 cm³ of ethanol, 5 cm³ of 2 N aqueous potassium hydroxide solution and 7 cm³ of water is heated at a temperature close to 80° C. for 1 hour. After adding 5.8 cm³ of a 10% aqueous solution of acetic acid, the precipitate obtained is drained and washed with 3 times 5 cm³ of water. After recrystallizing twice from a mixture of 7.5 cm³ of and ethanol 7.5 cm³ of dimethylformamide each time, 0.4 g of a yellow solid melting at 250° C. is obtained

REFERENCE EXAMPLE 29

A suspension of 1.17 g of 3-ethoxycarbonyl-7,8-difluoro-1-methoxy-4-oxo-1,4-dihydro-benzo[b][1,8-]naphthyridine and 0.7 g of 1-methylpiperazine in 15 cm³ of dimethyl sulphoxide is heated at a temperature close to 95° C. for 30 minutes. After cooling to a temperature close to 20° C., the reaction mixture is poured into 60 cm³ of water and the mixture is extracted with 3 times 25 cm³ of trichloromethane. The combined organic extracts are washed with 3 times 25 cm³ of water, dried over magnesium sulphate, filtered and concentrated under reduced pressure (20 kPa) at a temperature close to 50° C. The solid obtained is taken up in 10 cm³ of diisopropyl ether, drained and washed with 5 cm³ of the same solvent. After recrystallizing from 90 cm³ of ethanol, 1.18 g of 3-ethoxycarbonyl-7-fluoro-1-methoxy-8-(4-methyl-1-piperazinyl)-4-oxo-1,4-dihydro-benzo[b][1,8]naphthyridine are obtained in the form of a yellow solid melting at 230° C.

A suspension of 0.98 g of 3-ethoxycarbonyl-7-fluoro-1-methoxy-8-(4-methyl-1-piperazinyl)-4-oxo-1,4-dihydro-benzo[b][1,8]naphthyridine in 15 cm³ of ethanol, 9 cm³ water and 6 cm³ of 2 N aqueous potassium hydroxide solution is stirred at a temperature close to 20° C. for 1 hour 6 cm³ of 2 N methanesulphonic acid are added to the solution obtained and the mixture is extracted with 3 times 10 cm³ of trichloromethane. The combined organic extracts are washed with 3 times 5 cm³ of water, dried over magnesium sulphate, filtered and concentrated to dryness under reduced pressure (20 kPa) at about 50° C. The dry extract obtained is taken up in 5 cm³ of diisopropyl ether, drained and washed with twice 2 cm³ of the same solvent. After recrystallizing once from 30 cm³ of dimethylformamide containing 30% of ethanol, 0.3 g of 7-fluoro-1-methoxy-8-(4-methyl-1-piperazinyl)-4-oxo-1,4-dihydro-benzo[b][1,8]-naphthyridine-3-carboxylic acid is obtained in the form of a brown solid melting at 270° C.

REFERENCE EXAMPLE 30

A suspension of 4 g of 3-ethoxycarbonyl-7,8,9-trifluoro-1-methyl-4-oxo-1,4-dihydro-benzo[b][1,8]naphthyridine in 30 cm³ of acetic acid and 30 cm³ of 50% hydrochloric acid is heated at a temperature close to 100° C. for 2 hours. After cooling to about 20° C., 100 cm³ of water are added. The precipitate formed is drained, washed with 3 times 50 cm³ of water and recrystallized from 80 cm³ of dimethylformamide. 3.4 g of 7,8,9-trifluoro-1-methyl-4-oxo-1,4-dihydro-benzo[b][1,8]naphthyridine-3-carboxylic acid are obtained in the form of a colourless solid melting at 350°-352° C.

A suspension of 4 g of 7,8,9-trifluoro-1-methyl-4-oxo-1,4-dihydro-benzo[b][1,8]naphthyridine-3-carboxylic acid in 60 cm³ of dimethyl sulphoxide and 3 g of 1-methylpiperazine is heated at 80° C. for 1 hour and a half. After cooling to about 20° C., 150 cm³ of water are added. 18 cm³ of 10% acetic acid are added to the solution obtained. The precipitate formed is drained, washed with 3 times 50 cm³ of water and recrystallized from 50 cm³ of dimethylformamide. 4 g of 7,9-difluoro-1-methyl-8-(4-methyl-1-piperazinyl)-4-oxo-1,4-dihydro-benzo[b][1,8]naphthyridine-3-carboxylic acid are obtained in the form of a yellow solid melting at 316° C.

REFERENCE EXAMPLE 31

A suspension of 2 g of 3-ethoxycarbonyl-7,8,9-trifluoro-1-methyl-4-oxo-1,4-dihydro-benzo[b][1,8]naphthyridine in 30 cm³ of dimethyl sulphoxide and 5 g of 2-methylpiperazine is heated at a temperature close to 100° C., with stirring, for 2 hours. The solution obtained is poured, at this temperature, with stirring, into a mixture of 150 cm³ of water and 50 g of ice. 5 g of potassium carbonate are added at about 20° C. and the mixture is extracted with 3 times 50 cm³ of trichloromethane. The combined organic extracts are washed with twice 50 cm: of water, dried over magnesium sulphate, filtered and concentrated to dryness under reduced pressure (20 kPa) at about 50° C. The residue obtained is recrystallized from 30 cm³ of ethanol. 1.6 g of (RS)-3-ethoxycarbonyl-7,9-difluoro-1-methyl-8-(3-methyl-1-piperazinyl)-4-oxo-1,4-dihydro-benzo[b][1,8]naphthyridine are obtained in the form of a yellow solid melting at 240° C.

A suspension of 1.5 g of (RS)-3-ethoxycarbonyl-7,9-difluoro-1-methyl-8-(3-methyl-1-piperazinyl)-4-oxo-1,4-dihydro-benzo[b][1,8]naphthyridine in 20 cm³ of ethanol and 20 cm³ of N aqueous potassium hydroxide solution is heated at a temperature close to 75° C. for 1 hour and a half. 12 g of a 10% aqueous solution of acetic acid is added to the solution obtained, at this latter temperature. The insoluble matter obtained is drained at about 75° C. and washed 3 times with 30 cm³ of water at about 20° C. After recrystallizing once from 100 cm³ of dimethylformamdide, 0.9 g of (RS)-7,9-difluoro-1-methyl-8-(3-methyl-1-piperazinyl)-4-oxo-1,4-dihydro-benzo[b][1,8]naphthyridine-3-carboxylic acid is obtained in the form of a yellow solid melting at 380°-382° C.

REFERENCE EXAMPLE 32

Carrying out the reaction under the conditions of Reference Example 31, but starting from 1.75 g of 3-ethoxycarbonyl-1-ethyl-7,8,9-trifluoro-4-oxo-1,4-dihydro-benzo[b][1,8]naphthyridine and 4.3 g of piperazine, 1.1 g of 3-ethoxycarbonyl-1-ethyl-7,9-difluoro-4-oxo-8-(1-piperazinyl)-1,4-dihydro-benzo[b][1,8]naphthyridine are obtained in the form of a yellow solid melting at 229° C.

Carrying out the reaction under the conditions of Reference Example 31, but starting from 1 g of 3-ethoxycarbonyl-1-ethyl-7,9-difluoro-4-oxo-8-(1-piperazinyl)-1,4-dihydro-benzo[b][1,8]naphthyridine, 0.7 g of 1-ethyl-7,9-difluoro-4-oxo-8-(1-piperazinyl)-1,4-dihydro-benzo[b][1,8]naphthyridine-3-carboxylic acid is obtained in the form of a yellow solid melting at 340°-342° C.

REFERENCE EXAMPLE 33

The reaction is carried out under the conditions described in Reference Example 31, but starting from 1.9 g of 3-ethoxycarbonyl-7,8,9-trifluoro-4-oxo-1-tert.-butyl-1,4-dihydro-benzo[b][1,8]naphthyridine and 4.3 g of piperazine. After recrystallizing once from 50 cm³ of diisopropyl ether and 10 cm³ of propan-2-ol, 2 g of 3-ethoxycarbonyl-7,9-difluoro-4-oxo-8-(1-piperazinyl)-1-tert.-butyl-1,4-dihydro-benzo[b][1,8]naphthyridine are obtained in the form of a yellow solid melting at 186° C.

Carrying out the reaction under the conditions described above in Reference Example 31, but starting from 2 g of 3-ethoxycarbonyl-7,9-difluoro-4-oxo-8-(1-piperazinyl)-1-tert.-butyl-1,4-dihydro-benzo[b][1,8-]naphthyridine. After recrystallizing from 35 cm³ of dimethylformamide and 35 cm³ of ethanol, 1 g of 7,9-difluoro-4-oxo-8-(1-piperazinyl)-1-tert.-butyl-1,4-dihydro-benzo[b][1,8]naphthyridine-3-carboxylic acid is obtained in the form of a yellow solid melting at 318° C.

REFERENCE EXAMPLE 34

The reaction is carried out under the conditions of Reference Example 31, but starting from 1.8 g of 1-cyclopropyl-3-ethoxycarbonyl-7,8,9-trifluoro-4-oxo-1,4-dihydro-benzo[b][1,8]naphthyridine and 2 g of (RS)-2-methylpiperazine. After recrystallizing once from 15 cm³ of propan-2-ol and 15 cm³ of diisopropyl ether, 1.9 g of (RS)-1-cyclopropyl-3-ethoxycarbonyl-7,9-difluoro-8-(3-methyl-1-piperazinyl)-4-oxo-1,4-dihydro-benzo[b][1,8]naphthyridine are obtained in the form of a yellow solid melting at 190° C.

The reaction is carried out under the conditions of Reference Example 31, but starting from 1.9 g of (RS)-1-cyclopropyl-3-ethoxycarbonyl-7,9-difluoro-8-(3-methyl-1-piperazinyl)-4-oxo-1,4-dihydro-benzo[b][1,8-]naphthyridine. After recrystallizing once from a mixture of 20 cm³ of dimethylformamide and 20 cm³ of ethanol, 1.1 g of (RS)-1-cyclopropyl-7,9-difluoro-8-(3-methyl-1-piperazinyl)-4-oxo-1,4-dihydro-benzo[b][1,8-]naphthyridine-3-carboxylic acid are obtained in the form of a yellow solid melting at 309° C.

REFERENCE EXAMPLE 35

The reaction is carried out as described above in Reference Example 30, but starting from 9 g of 3-ethoxycarbonyl-6,7,8-trifluoro-1-methoxy-4-oxo-1,4-dihydro-benzo[b][1,8]naphthyridine. 7.7 g of 6,7,8-trifluoro-1-methoxy-4-oxo-1,4-dihydro-benzo[b][1,8]-naphthyridine-3-carboxylic acid are obtained in the form of a beige solid melting at 322° C.

A suspension of 2 g of 6,7,8-trifluoro-1-methoxy-4-oxo-1,4-dihydro-benzo[b][1,8]naphthyridine-3-carboxylic acid and 2.8 g of piperazine in 40 cm³ of dimethyl sulphoxide is heated, with stirring, at about 50° C. for 45 minutes. After cooling to a temperature close to 20° C., the suspension obtained is poured into 100 cm³ of water and 9.22 g of methanesulphonic acid are added. A small amount of insoluble matter is removed by filtration through diatomaceous silica. 32 cm³ of 2N aqueous potassium hydroxide solution are added to the filtrate. The precipitate obtained is drained, washed with 3 times 50 cm³ of water and recrystallized from 80 cm³ of dimethylformamide. 1.4 g of 7,9-difluoro-1-methoxy-4-oxo-8-(1-piperazinyl)-1,4-dihydro-benzo[b][1,8]naphthyridine-3-carboxylic acid are obtained in the form of a yellow solid melting at 305°-308° C.

We claim:

1. A benzo[b][1,8]naphthyridine derivative, comprising that it corresponds to the formula:

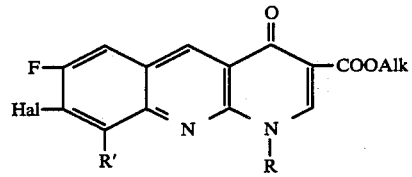

in which:
R represents a hydrogen atom or an alkyl or fluoroalkyl radical, a cycloalkyl radical containing 3 to 6 carbon atoms, or an alkoxy, alkylamino or protected alkylamino radical,
Hal represents a fluorine, chlorine or bromine atom if R' is a hydrogen atom, or Hal and R' simultaneously represent a fluorine atoms, and
Alk represents an alkyl radical,
the alkyl radicals having 1 to 4 carbon atoms in a straight or branched chain.

2. A benzo[b][1,8]naphthyridine derivative according to claim 1, wherein
R is a hydrogen atom, an alkyl radical having 1 to 4 carbon atoms in a straight or branched chain, fluoroethyl, cyclopropyl, methoxy or protected methylamino,
Hal is a fluorine or chlorine atom and
R' is a hydrogen atom, or
Hal and R' are simultaneously fluorine atoms and
Alk is an ethyl radical.

3. 8-Chloro-3-ethoxycarbonyl-7-fluoro-b 1-methyl-4-oxo-1,4-dihydro-benzo [b][1.8]naphthyridine.

4. 3-Ethoxycarbonyl-7,8-difluoro-1-methyl-4-oxo-1,4-dihydro-benzo [b][1,8]naphthyridine.

5. 3-Ethoxycarbonyl-7,8-difluoro-1-methoxy-4-oxo-1,4-dihydro-benzo [b][1,8]naphthyridine.

6. 3-Ethoxycarbonyl-1-cyclopropyl-7,8-difluoro-4-oxo-1,4-dihydro-benzo [b][1.8]naphthyridine.

7. 3-Ethoxycarbonyl-1-methyl-4-oxo-7,8,9-trifluoro-1,4-dihydro-benzo [b][1,8]naphthyridine.

* * * * *